US012805912B2

(12) United States Patent
Jackson et al.

(10) Patent No.: US 12,805,912 B2
(45) Date of Patent: Nov. 24, 2026

(54) BONE ANCHOR RECEIVER WITH HORIZONTALLY-ELONGATED TOOL ENGAGEMENT GROOVES

(71) Applicant: Roger P. Jackson, Prairie Village, KS (US)

(72) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 0 days.

(21) Appl. No.: 19/409,290

(22) Filed: Dec. 4, 2025

(65) Prior Publication Data

US 2026/0083482 A1 Mar. 26, 2026

Related U.S. Application Data

(60) Continuation of application No. 19/341,930, filed on Sep. 26, 2025, which is a division of application No.
(Continued)

(51) Int. Cl.
*A61B 17/70* (2006.01)
*A61B 17/86* (2006.01)
(Continued)

(52) U.S. Cl.
CPC ...... *A61B 17/7037* (2013.01); *A61B 17/7005* (2013.01); *A61B 17/7008* (2013.01);
(Continued)

(58) Field of Classification Search
CPC ............ A61B 17/7032; A61B 17/7034; A61B 17/7035; A61B 17/7037
See application file for complete search history.

(56) References Cited

U.S. PATENT DOCUMENTS 944,847 A 12/1909 Cochius
5,443,467 A 8/1995 Biedermann et al.
(Continued)

OTHER PUBLICATIONS

Depuyspine, Expedium Spine System Product Catalog, 2004, 20 pages.

*Primary Examiner* — Ellen C Hammond
(74) *Attorney, Agent, or Firm* — Polsinelli PC

(57) ABSTRACT

A receiver of a bone anchor assembly includes a receiver body having a base portion and a pair of upright arms defining a channel for receiving a rod, the upright arms having top surfaces, opposed interior surfaces, and exterior side surfaces extending downward across the upright arms and base portion to a bottom of the receiver body. The receiver also includes a horizontally-elongate upper tool-engaging groove formed into the exterior side surface of each upright arm proximal to and below the top surface of the upright arm, extending horizontally to at least a front face or a back face of the upright arm, and including a downwardly-facing upper surface, an upwardly-facing lower surface, and an outwardly-facing inner surface. The receiver further includes a tool-engaging recess extending across the upper tool-engaging groove of each upright arm, with the tool-engaging recess extending upwardly through the downwardly-facing upper surface and downwardly through the upwardly-facing lower surface and including an outwardly-facing planar surface opposite and parallel to an outwardly-facing planar surface of the tool-engaging recess of the other upright arm.

33 Claims, 16 Drawing Sheets

Related U.S. Application Data

18/462,275, filed on Sep. 6, 2023, now Pat. No. 12,440,245, which is a continuation of application No. 17/933,430, filed on Sep. 19, 2022, now Pat. No. 11,751,916, which is a continuation of application No. 17/473,060, filed on Sep. 13, 2021, now Pat. No. 11,464,548, which is a continuation of application No. 17/129,281, filed on Dec. 21, 2020, now Pat. No. 11,116,548, which is a continuation of application No. 16/227,382, filed on Dec. 20, 2018, now Pat. No. 10,869,694, which is a continuation of application No. 15/878,542, filed on Jan. 24, 2018, now Pat. No. 10,172,649, which is a continuation-in-part of application No. 15/338,817, filed on Oct. 31, 2016, now Pat. No. 9,883,892, which is a continuation of application No. 13/573,874, filed on Oct. 10, 2012, now Pat. No. 9,480,517, which is a continuation-in-part of application No. 13/573,516, filed on Sep. 19, 2012, now Pat. No. 9,918,745, and a continuation-in-part of application No. 13/573,303, filed on Sep. 7, 2012, now Pat. No. 9,393,047, and a continuation-in-part of application No. 13/506,365, filed on Apr. 13, 2012, now Pat. No. 8,444,681, and a continuation-in-part of application No. 13/374,439, filed on Dec. 29, 2011, now Pat. No. 9,980,753, and a continuation-in-part of application No. 13/373,289, filed on Nov. 9, 2011, now Pat. No. 9,907,574, and a continuation-in-part of application No. 12/924,802, filed on Oct. 5, 2010, now Pat. No. 8,556,938, and a continuation-in-part of application No. 12/802,849, filed on Jun. 15, 2010, now abandoned.

(60) Provisional application No. 61/627,374, filed on Oct. 11, 2011, provisional application No. 61/626,250, filed on Sep. 23, 2011, provisional application No. 61/573,508, filed on Sep. 7, 2011, provisional application No. 61/517,088, filed on Apr. 13, 2011, provisional application No. 61/463,037, filed on Feb. 11, 2011, provisional application No. 61/460,234, filed on Dec. 29, 2010, provisional application No. 61/460,267, filed on Dec. 29, 2010, provisional application No. 61/456,649, filed on Nov. 10, 2010, provisional application No. 61/403,915, filed on Sep. 23, 2010, provisional application No. 61/403,696, filed on Sep. 20, 2010, provisional application No. 61/402,959, filed on Sep. 8, 2010, provisional application No. 61/400,504, filed on Jul. 29, 2010, provisional application No. 61/398,807, filed on Jul. 1, 2010, provisional application No. 61/396,390, filed on May 26, 2010, provisional application No. 61/395,752, filed on May 17, 2010, provisional application No. 61/395,564, filed on May 14, 2010, provisional application No. 61/343,737, filed on May 3, 2010, provisional application No. 61/336,911, filed on Jan. 28, 2010, provisional application No. 61/278,240, filed on Oct. 5, 2009, provisional application No. 61/270,754, filed on Jul. 13, 2009, provisional application No. 61/268,708, filed on Jun. 15, 2009.

(51) Int. Cl.

| | |
|---|---|
| *A61B 17/56* | (2006.01) |
| *A61B 17/68* | (2006.01) |
| *A61B 90/00* | (2016.01) |

(52) U.S. Cl.

CPC ........ *A61B 17/702* (2013.01); *A61B 17/7032* (2013.01); *A61B 17/7034* (2013.01); *A61B 17/7035* (2013.01); *A61B 17/7038* (2013.01); *A61B 17/7082* (2013.01); *A61B 17/7091* (2013.01); *A61B 17/864* (2013.01); *A61B 2017/567* (2013.01); *A61B 2017/681* (2013.01); *A61B 2090/0808* (2016.02); *Y10T 29/49826* (2015.01)

(56) References Cited

U.S. PATENT DOCUMENTS

| | | | |
|---|---|---|---|
| 5,879,350 | A | 3/1999 | Sherman et al. |
| 6,010,503 | A | 1/2000 | Richelsoph et al. |
| 6,074,391 | A | 6/2000 | Metz-Stavenhagen |
| 6,077,262 | A | 6/2000 | Schläpfer et al. |
| 6,540,749 | B2 | 4/2003 | Schäfer et al. |
| 6,554,834 | B1 | 4/2003 | Crozet et al. |
| 6,648,888 | B1 | 11/2003 | Shluzas |
| 6,835,196 | B2 | 12/2004 | Biedermann et al. |
| 7,160,300 | B2 | 1/2007 | Jackson |
| 7,179,261 | B2 | 2/2007 | Sicvol et al. |
| 7,214,227 | B2 | 5/2007 | Colleran et al. |
| 7,250,052 | B2 | 7/2007 | Landry et al. |
| 7,316,684 | B1 | 1/2008 | Baccelli et al. |
| 7,479,156 | B2 | 1/2009 | Lourdel et al. |
| 7,527,638 | B2 | 5/2009 | Anderson et al. |
| 7,588,575 | B2 | 9/2009 | Colleran et al. |
| 7,588,588 | B2 | 9/2009 | Spitler et al. |
| 7,621,918 | B2 | 11/2009 | Jackson |
| 7,666,188 | B2 | 2/2010 | Anderson et al. |
| 7,766,915 | B2 | 8/2010 | Jackson |
| 7,776,067 | B2 | 8/2010 | Jackson |
| 7,862,587 | B2 | 1/2011 | Jackson |
| 7,951,172 | B2 | 5/2011 | Chao et al. |
| 7,967,850 | B2 | 6/2011 | Jackson |
| 7,972,364 | B2 | 7/2011 | Biedermann et al. |
| 7,988,694 | B2 | 8/2011 | Barrus et al. |
| 8,066,739 | B2 | 11/2011 | Jackson |
| 8,328,817 | B2 | 12/2012 | Strauss |
| 8,353,932 | B2 | 1/2013 | Jackson |
| 8,361,123 | B2 | 1/2013 | Fanger et al. |
| 8,444,681 | B2 | 5/2013 | Jackson et al. |
| 8,556,938 | B2 | 10/2013 | Jackson et al. |
| 8,628,558 | B2 | 1/2014 | Harvey et al. |
| 8,657,858 | B2 | 2/2014 | Garamszegi et al. |
| 8,663,290 | B2 | 3/2014 | Doubler et al. |
| 8,663,298 | B2 | 3/2014 | Keyer et al. |
| 8,876,869 | B1 | 11/2014 | Schafer et al. |
| 8,926,671 | B2 | 1/2015 | Biedermann et al. |
| 8,998,959 | B2 | 4/2015 | Jackson et al. |
| 9,050,148 | B2 | 6/2015 | Jackson |
| 9,119,674 | B2 | 9/2015 | Matthis et al. |
| 9,168,069 | B2 | 10/2015 | Jackson et al. |
| 9,198,695 | B2 | 12/2015 | Shluzas et al. |
| 9,480,517 | B2 | 11/2016 | Jackson et al. |
| 9,907,574 | B2 | 3/2018 | Jackson et al. |
| 9,918,745 | B2 | 3/2018 | Jackson et al. |
| 9,980,753 | B2 | 5/2018 | Jackson et al. |
| 10,172,647 | B2 | 1/2019 | Elsbury |
| 10,792,074 | B2 | 10/2020 | Jackson |
| 2004/0181224 | A1 | 9/2004 | Biedermann et al. |
| 2004/0186473 | A1 | 9/2004 | Cournoyer et al. |
| 2011/0040335 | A1 | 2/2011 | Stihl et al. |
| 2013/0103098 | A1 | 4/2013 | Jackson |

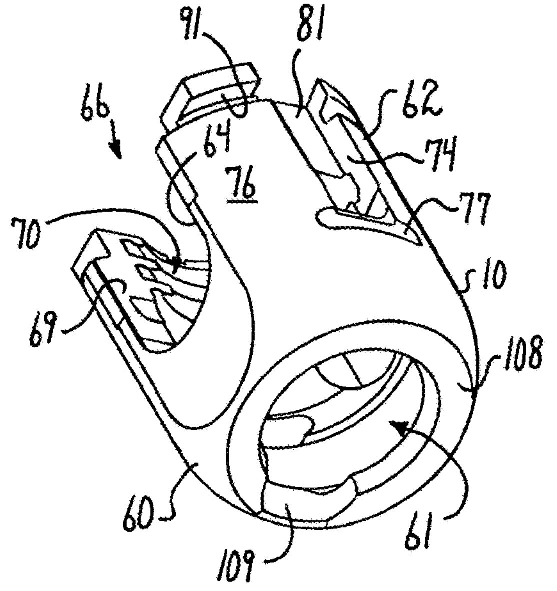
Fig. 8.
Fig. 9.
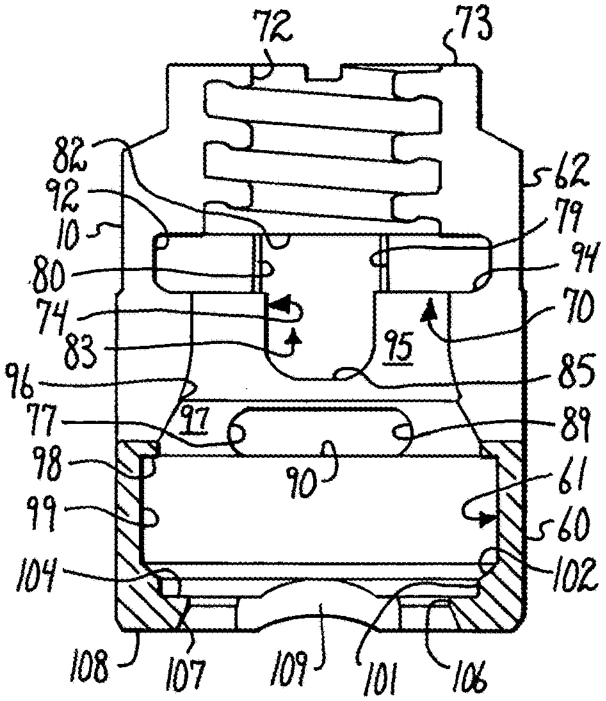
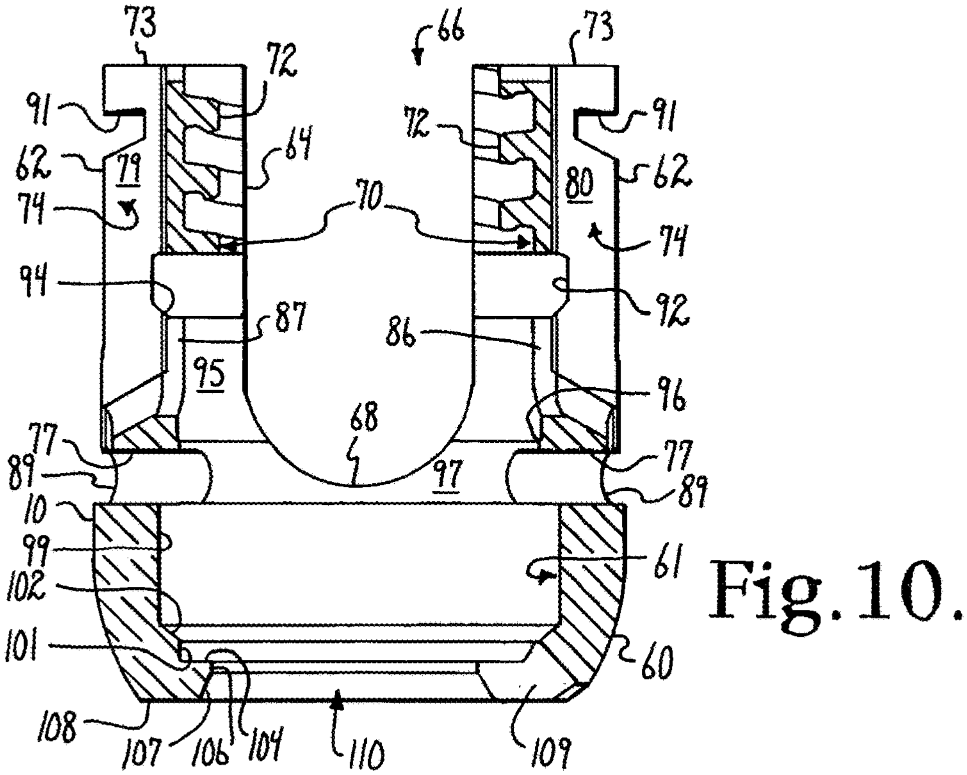
Fig.10.

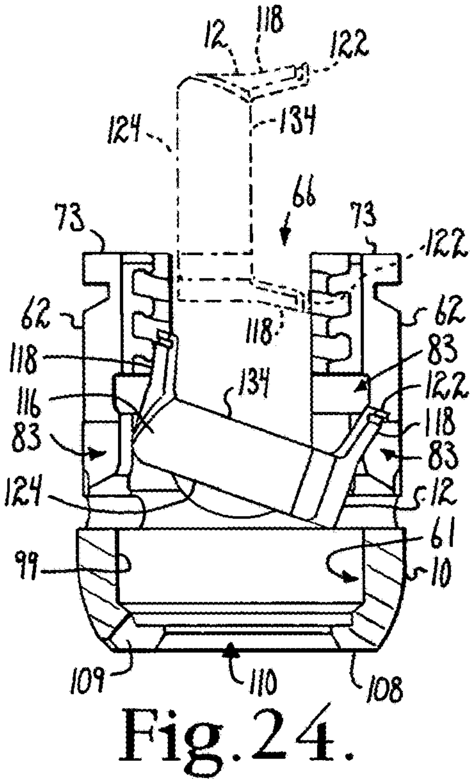
Fig. 24.
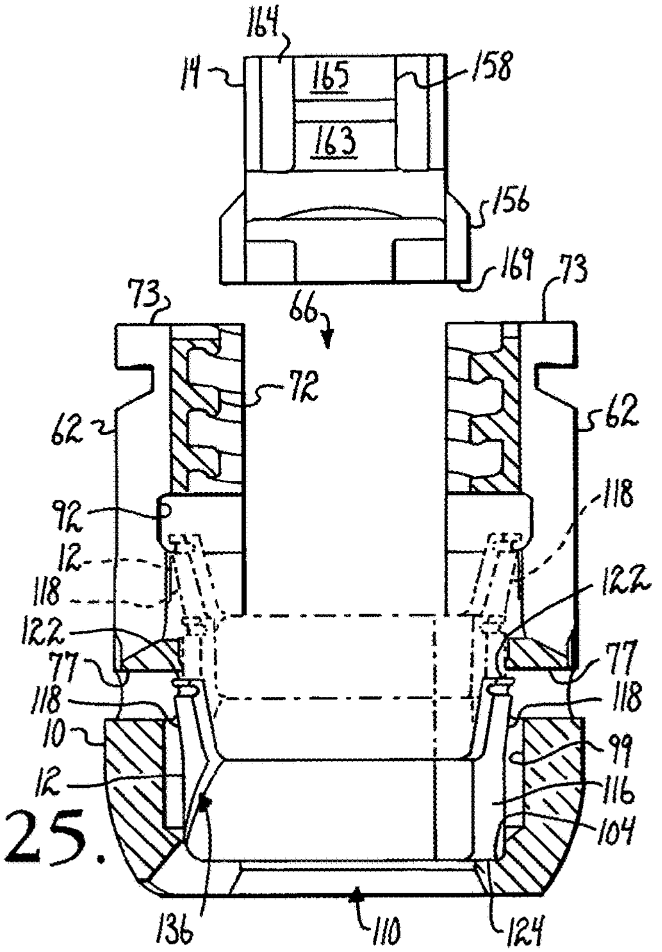
Fig. 25.
Fig. 26.
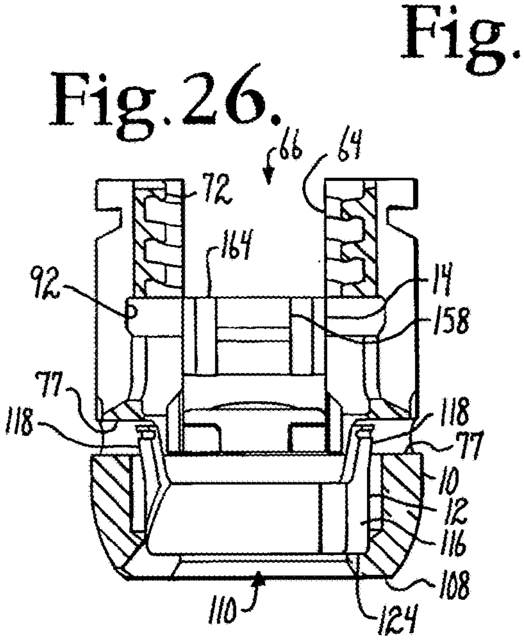
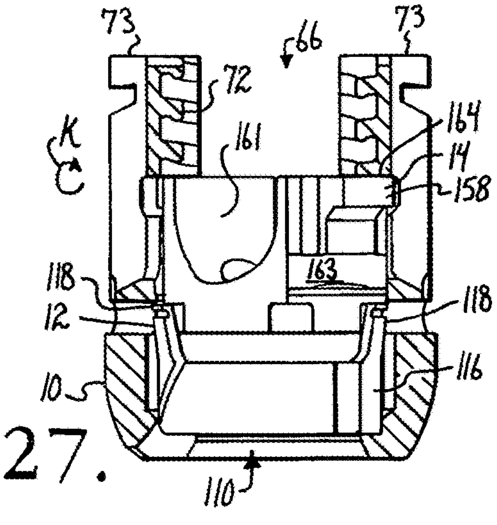
Fig. 27.

Fig.28.
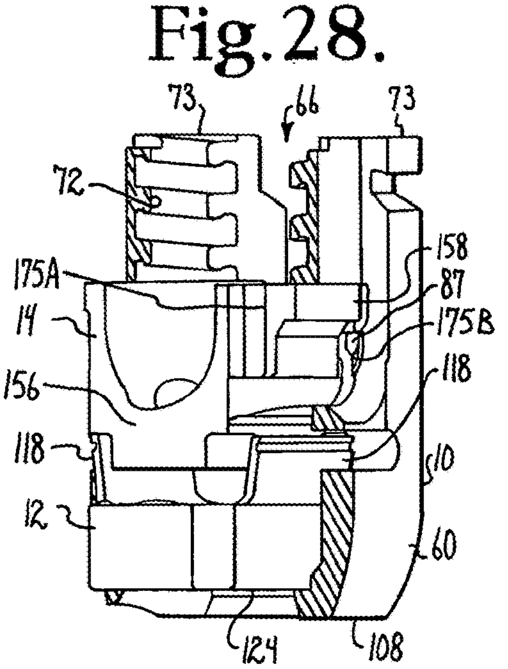
Fig.29.
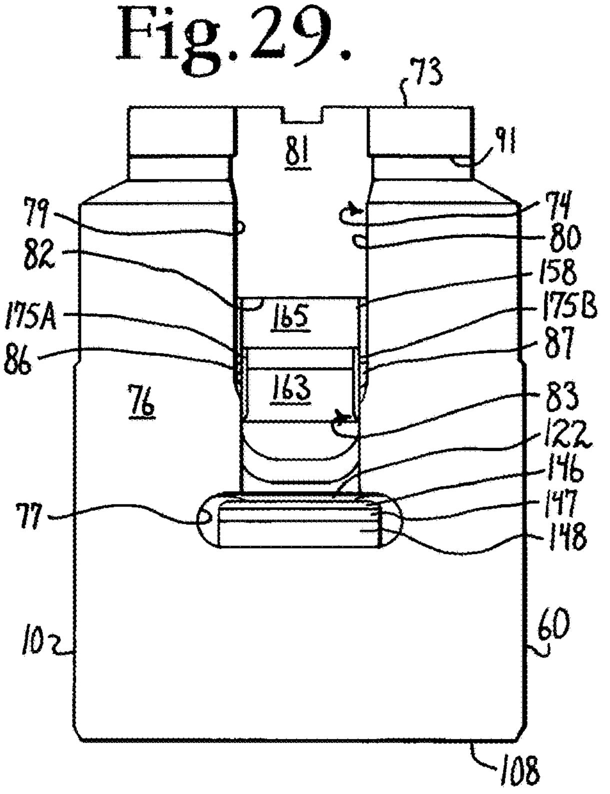
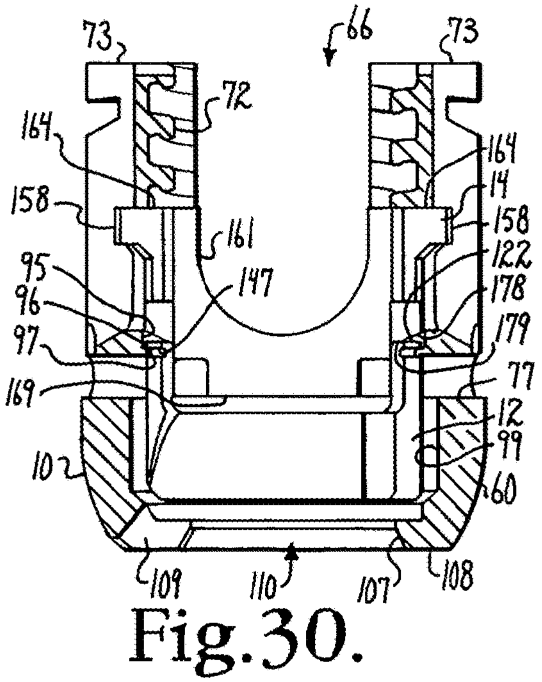
Fig.30.
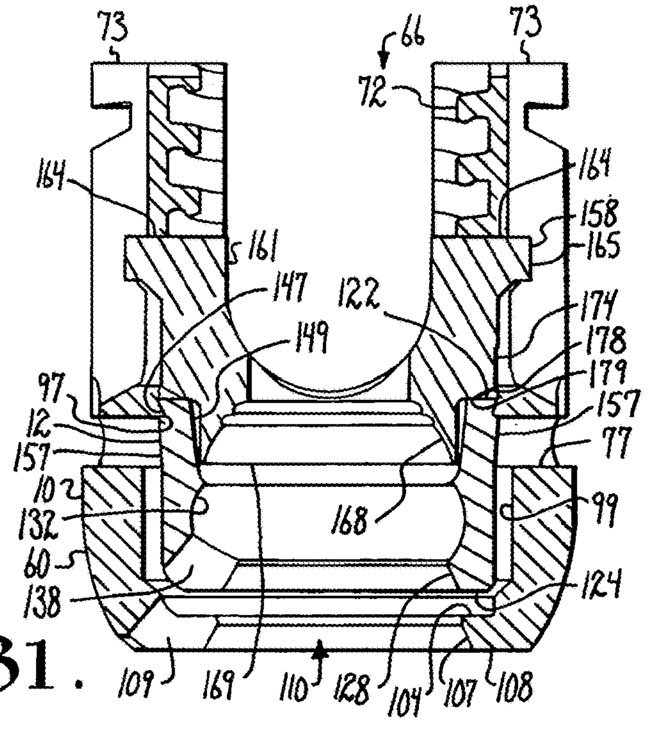
Fig.31.

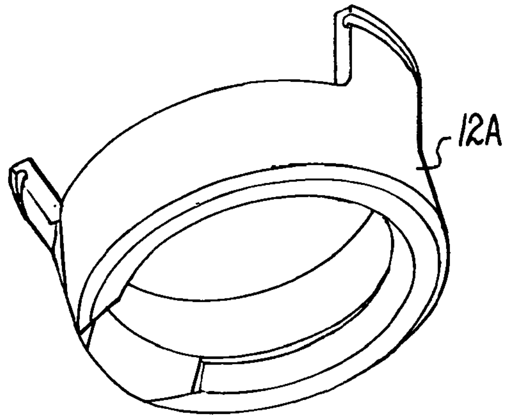
Fig. 47.
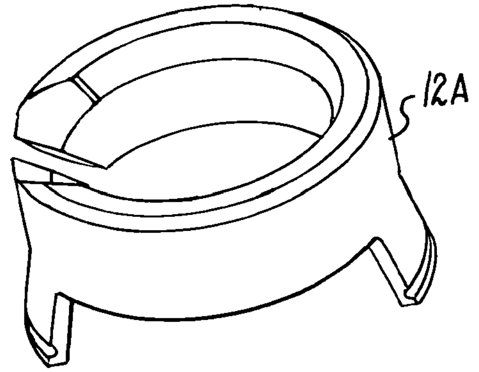
Fig. 48.
Fig. 49.
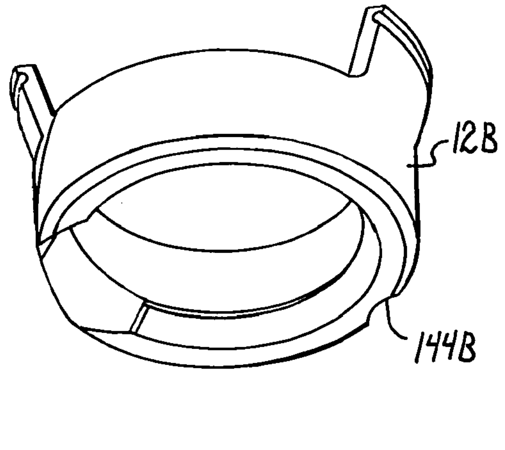
Fig. 50.
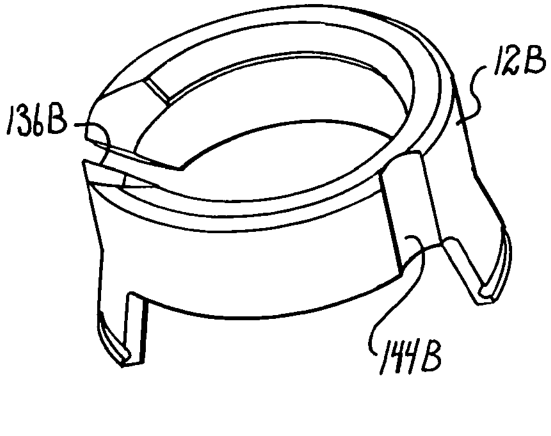

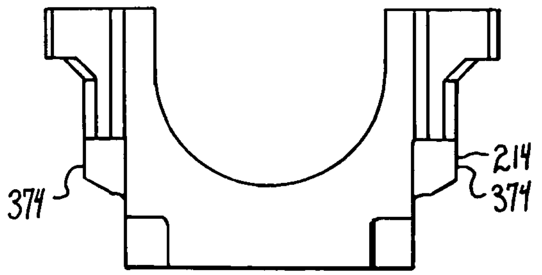
Fig. 55.
Fig. 56.
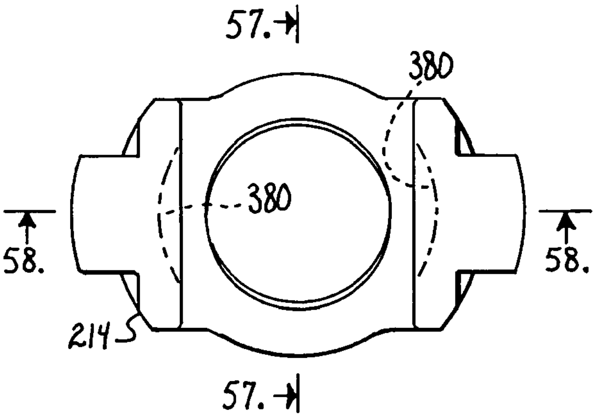
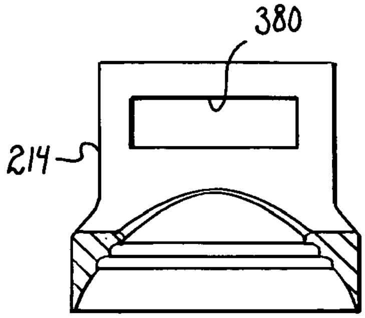
Fig. 57.
Fig. 58.
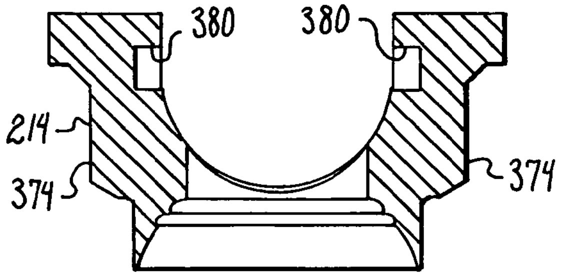

BONE ANCHOR RECEIVER WITH HORIZONTALLY-ELONGATED TOOL ENGAGEMENT GROOVES

CROSS-REFERENCE TO RELATED APPLICATIONS

This application is a continuation of U.S. application Ser. No. 19/341,930 filed Sep. 26, 2025, which is a divisional of U.S. application Ser. No. 18/462,275 filed Sep. 6, 2023, now U.S. Pat. No. 12,440,245, which is a continuation of U.S. application Ser. No. 17/933,430 filed Sep. 19, 2022, now U.S. Pat. No. 11,751,916, which is a continuation of U.S. application Ser. No. 17/473,060 filed Sep. 13, 2021, now U.S. Pat. No. 11,464,548, which is a continuation of U.S. application Ser. No. 17/129,281 filed Dec. 21, 2020, now U.S. Pat. No. 11,116,548, which is a continuation of U.S. application Ser. No. 16/227,382 filed Dec. 20, 2018, now U.S. Pat. No. 10,869,694, which is a continuation of U.S. application Ser. No. 15/878,542 filed Jan. 24, 2018, now U.S. Pat. No. 10,172,649, which is a continuation-in-part of U.S. application Ser. No. 15/338,817 filed Oct. 31, 2016, now U.S. Pat. No. 9,883,892, which is a continuation of U.S. application Ser. No. 13/573,874 filed Oct. 10, 2012, now U.S. Pat. No. 9,480,517, which claims the benefit of U.S. Provisional Application No. 61/627,374 filed Oct. 11, 2011, each of which is incorporated by reference in its entirety herein, and for all purposes.

U.S. application Ser. No. 13/573,874 is also a continuation-in-part of U.S. application Ser. No. 13/573,516 filed Sep. 19, 2012, now U.S. Pat. No. 9,918,745, which claims the benefit of U.S. Provisional Application No. 61/626,250 filed Sep. 23, 2011, each of which is incorporated by reference in its entirety herein, and for all purposes.

U.S. application Ser. No. 13/573,874 is also a continuation-in-part of U.S. application Ser. No. 13/573,303 filed Sep. 7, 2012, now U.S. Pat. No. 9,393,047, which claims the benefit of U.S. Provisional Application No. 61/573,508 filed Sep. 7, 2011, each of which is incorporated by reference in its entirety herein, and for all purposes.

U.S. application Ser. No. 13/573,874 is also a continuation-in-part of U.S. application Ser. No. 13/506,365 filed Apr. 13, 2012, now U.S. Pat. No. 8,444,681, which claims the benefit of U.S. Provisional Application No. 61/517,088 filed Apr. 13, 2011, each of which is incorporated by reference in its entirety herein, and for all purposes.

U.S. application Ser. No. 13/573,874 is also a continuation-in-part of U.S. application Ser. No. 13/374,439 filed Dec. 29, 2011, now U.S. Pat. No. 9,980,753, which claims the benefit of U.S. Provisional Application No. 61/460,267 filed Dec. 29, 2010 and U.S. Provisional Application No. 61/463,037 filed Feb. 11, 2011, each of which is incorporated by reference in its entirety herein, and for all purposes.

U.S. application Ser. No. 13/573,874 is also a continuation-in-part of U.S. application Ser. No. 13/373,289 filed Nov. 9, 2011, now U.S. Pat. No. 9,907,574, which claims the benefit of U.S. Provisional Application No. 61/456,649 filed Nov. 10, 2010 and U.S. Provisional Application No. 61/460,234 filed Dec. 29, 2010, each of which is incorporated by reference in its entirety herein, and for all purposes.

U.S. application Ser. No. 13/573,874 is also a continuation-in-part of U.S. application Ser. No. 12/924,802 filed Oct. 5, 2010, now U.S. Pat. No. 8,556,938, which claims the benefit of U.S. Provisional Application Nos. 61/278,240 filed Oct. 5, 2009; 61/336,911 filed Jan. 28, 2010; 61/343,737 filed May 3, 2010; 61/395,564 filed May 14, 2010; 61/395,752 filed May 17, 2010; 61/396,390 filed May 26, 2010; 61/398,807 filed Jul. 1, 2010; 61/400,504 filed Jul. 29, 2010; 61/402,959 filed Sep. 8, 2010; 61/403,696 filed Sep. 20, 2010; and 61/403,915 filed Sep. 23, 2010, each of which is incorporated by reference in its entirety herein, and for all purposes.

U.S. application Ser. No. 13/573,874 is also a continuation-in-part of U.S. application Ser. No. 12/802,849 filed Jun. 15, 2010, now abandoned, which claims the benefit of U.S. Provisional Application Nos. 61/268,708 filed Jun. 15, 2009; 61/270,754 filed Jul. 13, 2009; 61/336,911 filed Jan. 28, 2010; 61/395,564 filed May 14, 2010; 61/395,752 filed May 17, 2010; and 61/396,390 filed May 26, 2010, each of which is incorporated by reference in its entirety herein, and for all purposes.

BACKGROUND OF THE INVENTION

The present invention is directed to polyaxial bone screws for use in bone surgery, particularly spinal surgery and particularly to such screws with compression or pressure inserts and expansion-only split retainers to snap over, capture and retain the bone screw shank head in the receiver member assembly and later fix the bone screw shank with respect to the receiver assembly.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible' to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult. Also, it is often desirable to insert the bone screw shank separate from the receiver or head due to its bulk which can get in the way of what the surgeon needs to do. Such screws that allow for this capability are sometimes referred to as modular polyaxial screws.

With specific reference to modular snap-on or pop-on polyaxial pedicle screw systems having shank receiver assemblies, the prior art has shown and taught the concept of the receiver and certain retainer parts forming an assembly wherein a contractile locking engagement between the parts is created to fix the shank head with respect to the receiver and retainer. The receiver and shank head retainer assemblies in the prior art have included a slotted contractile retainer ring and/or a lower pressure slotted insert with an expansion and contraction collet-type of structure having contractile locking engagement for the shank head due to direct contact between the retainer and/or the collet structure with the receiver resulting in contraction of the slotted retainer ring and/or the collet-type structure of the insert against the shank head. The receiver and slotted insert have generally included tapered locking engagement surfaces.

The prior art for modular polyaxial screw assemblies has also shown and taught that the contact surfaces on the outside of the slotted collet and/or retainer and the inside of the receiver, in addition to being tapered, can be conical, radiused, spherical, curvate, multi-curvate, rounded, as well as other configurations to create a contractile type of locking engagement for the shank head with respect to the receiver.

In addition, the prior art for modular polyaxial screw assemblies has shown and taught that the shank head can both enter and escape from a collet-like structure on the insert or from the retainer when the insert or retainer is in the up position and within an expansion recess or chamber of the receiver. This is the case unless the slotted insert and/or the slotted retainer are blocked or constrained from being able to be pushed or manipulated back up into receiver bore or cavity, or unless the screw assemblies are otherwise uniquely configured to prevent this from happening.

SUMMARY OF THE INVENTION

The present invention differentiates from the prior art by not allowing the receiver to be removed from the shank head once the parts are snapped-on and connected. This is true even if the retainer can go back up into the expansion chamber. This approach or design has been found to be more secure and to provide more resistance to pull-out forces compared to the prior art for modular polyaxial screw designs. Collect-like structures extending downwardly from lower pressure inserts, when used in modular polyaxial screw designs, as shown in the prior art, have been found to be somewhat weak with respect to pull-out forces encountered during some spinal reduction procedures. The present invention is designed to solve these problems.

The present invention also differentiates from all of the prior art by providing a split retainer ring with an inner radiused or partially spherical surface having a smaller radius than the shank upper portion that does not frictionally engage and thus does not participate in the locking engagement for the shank head with respect to the receiver. Rather upper and/or lower edges or surfaces that partially define the spherical surface frictionally engage the shank head to provide a desired non-floppy engagement the angle of the shank with respect to the retainer being manipulatable with some force. In addition, the retainer ring itself for the present invention is uniquely characterized by a base portion providing expansion to receive and capture the shank head and then having only expansion (not contraction) locking engagement between the shank head and the retainer ring base and between the retainer ring base and horizontal and vertical loading surfaces near a bottom opening of the receiver.

The expansion-only retainer ring base portion in the present invention is positioned entirely below the shank head hemisphere in the receiver and can be a stronger, more substantial structure to resist larger pull out forces on the assembly. The retainer ring base can also be better supported on a generally horizontal loading surface near the lower opening in the bottom of the receiver. This design has been found to be stronger and more secure when compared to that of the prior art which uses some type of contractile locking engagement between the parts, as described above; and, again, once assembled it cannot be disassembled.

Thus, a polyaxial bone screw assembly according to the invention includes a shank having an integral upper portion or integral radiused or spherical head and a body for fixation to a bone; a separate receiver defining an upper open channel, a central bore, a lower cavity and a lower opening; a top drop and turn in place lower compression insert; and a friction fit resilient expansion-only split retainer for capturing the shank head in the receiver lower cavity, the shank head being frictionally engaged with, but still movable in a non-floppy manner with respect to the friction fit retainer and the receiver prior to locking of the shank into a desired configuration. The compression insert further includes winged arm portions that extend outwardly through apertures in the receiver arms, providing for manipulation and seating of the retainer with respect to the receiver, and if desired, independent temporary locking of the insert against the shank. The shank is finally locked into a fixed position relative to the receiver by frictional engagement between the insert and a lower split ring-like portion of the retainer, as described previously, due to a downward force placed on the compression insert by a closure top pressing on a rod, or other longitudinal connecting member, captured within the receiver bore and channel. In the illustrated embodiments, retainers and compression inserts are downloaded into the receiver, but uploaded embodiments are also foreseen. The shank head can be positioned into the receiver lower cavity at the lower opening thereof prior to or after insertion of the shank into bone. In some embodiments, the compression insert may include a lock and release feature for independent locking of the polyaxial mechanism so the screw can be used like a fixed monoaxial screw. Also, in some embodiments the shank can be cannulated for minimally invasive surgery applications. The receiver can have crimp tabs, but is devoid of any type of spring tabs or collet-like structures. The lower pressure insert and/or the retainer are both devoid of any type of receiver-retainer contractile locking engagements with respect to the shank head, and again the receiver is devoid of any spring-tab like members. The retainer can also have upwardly extending spring tabs which are deployed into openings in the receiver cavity so that the retainer and captured shank head are stabilized and retained in the region of the receiver locking chamber once they enter into this lower portion of the receiver cavity. In this way, the shank head and retainer are constrained and cannot go back up into the receiver cavity.

Again, a pre-assembled receiver, compression insert and friction fit split retainer may be “pushed-on”, “snapped-on” or “popped-on” to the shank head prior to or after implantation of the shank into a vertebra. Such a “snapping on” procedure includes the steps of uploading the shank head into the receiver lower opening, the shank head pressing against the base portion of the split retainer ring and expanding the resilient lower open retainer portion out into an expansion portion or chamber of the receiver cavity followed by an elastic return of the retainer back to a nominal or near nominal shape thereof after the hemisphere of the shank head or upper portion passes through the lower ring-like portion of the retainer. The shank head enters into friction fit engagement with portions of the retainer, defined at least in part, by an inner curved surface or edge, such surface or edge having a radius smaller than a radius of the shank head surface being engaged by the retainer. The retainer snapping onto the shank head as the retainer returns to a neutral or close to neutral orientation, providing a non-floppy connection between the retainer and the shank head. In the illustrated embodiment, when the shank is ultimately locked between the compression insert and the lower portion of the retainer, only a lower surface defining the retainer radiused surface is required for locking engagement with the shank head. The final fixation occurs as a result of a locking expansion-type of contact between the shank head and the lower portion of the split retainer and an expansion-type of non-tapered locking engagement between the lower portion of the retainer ring and the locking chamber in the lower portion of the receiver cavity. The retainer can expand more in the upper portion or expansion chamber of the receiver cavity to allow the shank head to pass through, but has restricted expansion to retain the shank head when the retainer lower ring portion is against the locking chamber surfaces in the lower portion of the receiver cavity and the shank head is forced down against the retainer ring during final locking. In some embodiments, when the polyaxial mechanism is locked, the pressure or compression insert is forced or wedged against a surface of the receiver resulting in an interference locking engagement, allowing for adjustment or removal of the rod or other connecting member without loss of a desired angular relationship between the shank and the receiver. This independent locking feature allows the polyaxial screw to function like a fixed monoaxial screw.

The lower pressure insert may also be configured to be independently locked by a tool or instrument, thereby allowing the pop-on polyaxial screw to be distracted, compressed and/or rotated along and around the rod to provide for improved spinal correction techniques. Such a tool engages the receiver from the sides and then engages outwardly extending winged arms of the insert to force or wedge the insert down into a locked position within the receiver. With the tool still in place and the correction maintained, the rod is then locked within the receiver channel by a closure top followed by removal of the tool. This process may involve multiple screws all being manipulated simultaneously with multiple tools to achieve the desired correction.

It is noted that once the shank head is captured by the retainer ring and the retainer and head are moved down into the locking chamber region of the receiver cavity, retainer spring tabs are deployed outwardly stabilizing the retainer so that the retainer cannot go back up into the receiver cavity. This spring tab deployment also creates good rotational stability between the retainer and receiver and provides for an additional rotational friction fit between the shank head and the receiver itself since the retainer cannot axially rotate in the receiver. In this position, the retainer is fully constrained in the receiver with respect to translation, rotation and pivot.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 8 is another perspective view of the receiver of FIG. 4.

FIG. 9 is an enlarged cross-sectional view taken along the line 9-9 of FIG. 6.

FIG. 10 is an enlarged cross-sectional view taken along the line 10-10 of FIG. 6.

FIG. 24 is an enlarged front elevational view of the retainer and receiver of FIG. 1 with portions of the receiver broken away to show the detail thereof, the retainer being shown downloaded into the receiver (in phantom) to a partially inserted stage of assembly.

FIG. 25 is an enlarged front elevational view of the retainer and receiver with portions broken away, similar to what is shown in FIG. 24, showing the retainer in a subsequent stage of assembly (some intermediate stages in phantom) and further showing the insert of FIG. 1, in enlarged side elevation, just prior to being loaded into the receiver.

FIG. 26 is a reduced front elevational view of the retainer and receiver with portions broken away, similar to what is shown in FIG. 25, further showing the insert being downloaded into the receiver to a partially inserted stage of assembly.

FIG. 27 is a front elevational view with portions broken away, similar to FIG. 26, showing the insert being rotated within the receiver.

FIG. 28 is a perspective view, with portions broken away, of the receiver, retainer and insert of FIG. 27, the insert fully rotated into alignment with the receiver and further showing the receiver crimped to the insert.

FIG. 29 is an enlarged side elevational view of the receiver, retainer and insert of FIG. 28, also showing the receiver crimped to the insert.

FIG. 30 is an enlarged front elevational view with portions broken away, showing a subsequent stage of assembly to that shown in FIG. 28 with retainer spring tab arms being pressed toward one another and the retainer being moved upwardly within the receiver.

FIG. 31 is an enlarged front elevational view with portions broken away, showing a subsequent stage of assembly to that shown in FIG. 30, showing the retainer spring tab arms placed in a desired upward position within the receiver so that the retainer spring tabs push resiliently outwardly against the receiver, holding the retainer against the receiver and keeping the insert in an upward position during shipping.

FIG. 47 is an enlarged perspective view of an alternative retainer according to the invention for use with the assembly of FIG. 1.

FIG. 48 is another enlarged perspective view of the retainer of FIG. 47.

FIG. 49 is an enlarged perspective view of another alternative retainer according to the invention for use with the assembly of FIG. 1.

FIG. 50 is another enlarged perspective view of the retainer of FIG. 49.

FIG. 55 is an enlarged front elevational view of an alternative insert according to the invention for use with the assembly of FIG. 1 having outer independent lock-and-release surfaces and inner tool receiving slots.

FIG. 56 is a top plan view of the alternative insert of FIG. 55 with the inner tool receiving slots being shown in phantom.

FIG. 57 is a cross-sectional view taken along the line 57-57 of FIG. 56.

FIG. 58 is a cross-sectional view taken along the line 58-58 of FIG. 56.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Figure 1:
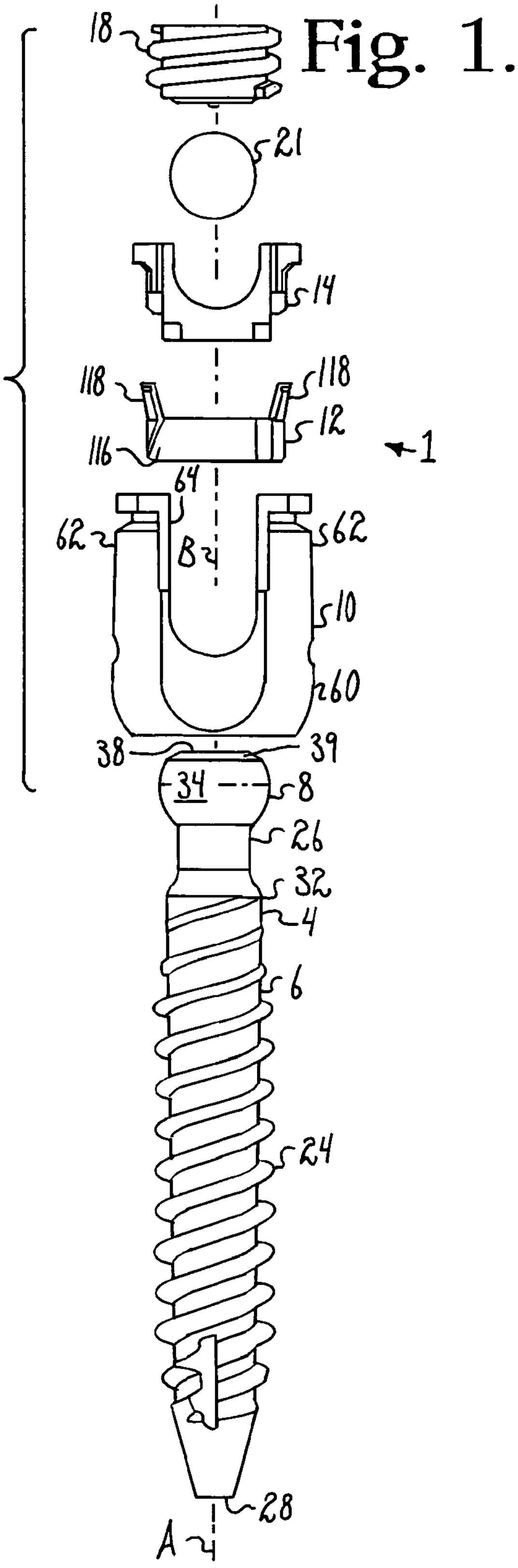
FIG. 1 is an exploded front elevational view of a polyaxial bone screw assembly according to the present invention including a shank, a receiver, an open friction fit expansion-only retainer and a top drop and turn in place lower compression insert, further shown with a portion of a longitudinal connecting member in the form of a rod and a closure top.
Figure 38:
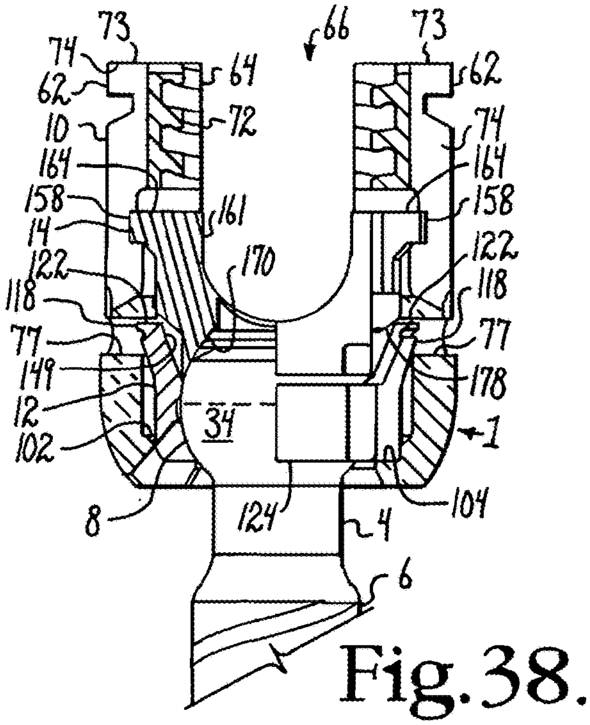
FIG. 38 is an enlarged and partial front elevational view with portions broken away, similar to FIG. 37, the retainer being shown pushed down into a fully seated position within the lower receiver cavity by pressure being placed thereon from above onto the insert, the insert further pressing the retainer spring tabs outwardly into the receiver apertures.
Figure 39:
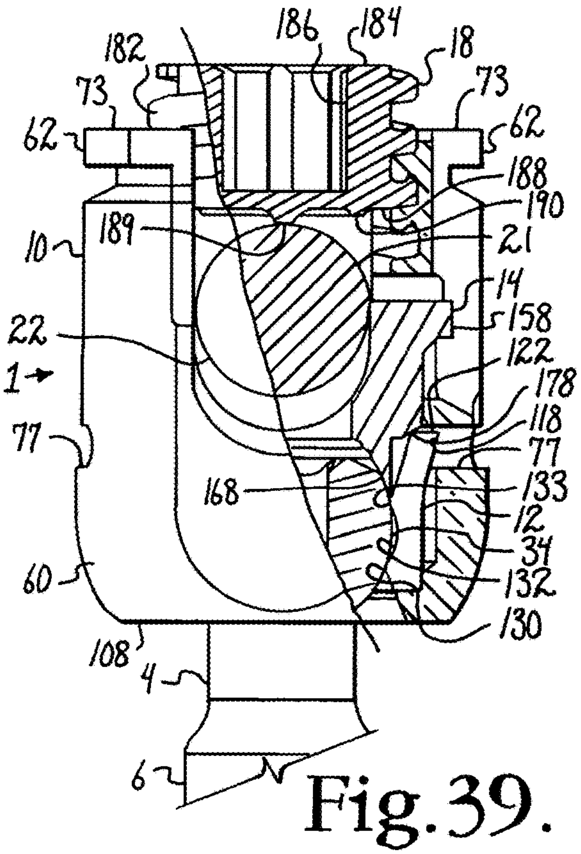
FIG. 39 is an enlarged and partial front elevational view with portions broken away of all of the components shown in FIG. 1, the assembly of FIG. 38 shown in an early stage of assembly with the rod and closure top.
Figure 40:
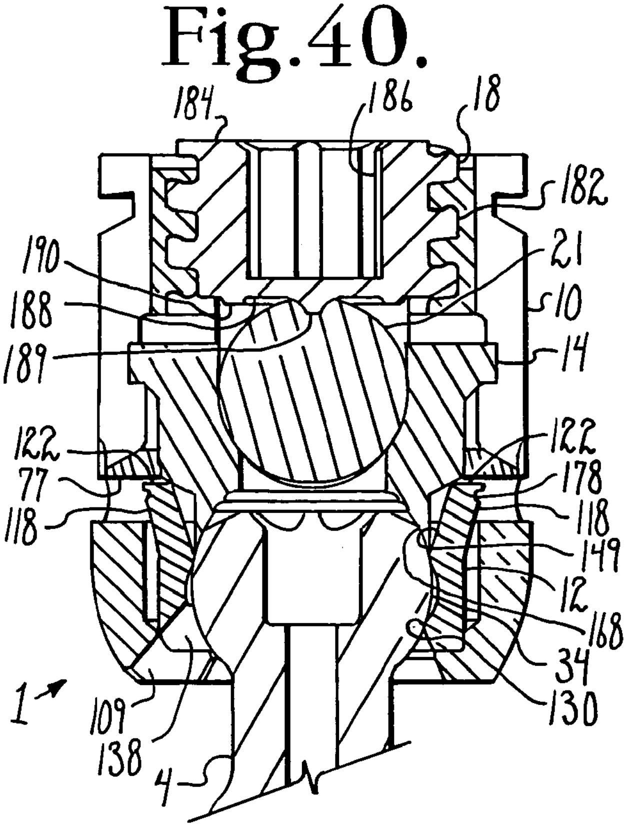
FIG. 40 is a partial front elevational view with portions broken away, similar to FIG. 39, shown in a final locking position.

With reference to FIGS. 1-46, the reference number 1 generally represents a polyaxial bone screw apparatus or assembly according to the present invention. The assembly 1 includes a shank 4, that further includes a body 6 integral with an upwardly extending upper portion or head structure 8; a receiver 10; a friction fit retainer 12, and a crown-like compression or pressure insert 14. The receiver 10, retainer 12 and compression insert 14 are initially assembled and may be further assembled with the shank 4 either prior or subsequent to implantation of the shank body 6 into a vertebra 17, as will be described in greater detail below. FIGS. 1 and 39-40 further show a closure structure 18 for capturing a longitudinal connecting member, for example, a rod 21 which in turn engages the compression insert 14 that presses against the shank upper portion 8 into fixed frictional contact with the retainer 12, so as to capture, and fix the longitudinal connecting member 21 within the receiver 10 and thus fix the member 21 relative to the vertebra 17. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The illustrated rod 21 is hard, stiff, non-elastic and cylindrical, having an outer cylindrical surface 22. It is foreseen that in other embodiments, the rod 21 may be elastic, deformable and/or of different materials and cross-sectional geometries. In such cases, the closure top could deform the rod and press directly on the insert 14.

Figure 2:
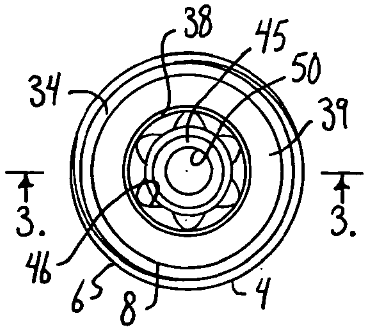
FIG. 2 is an enlarged top plan view of the shank of FIG. 1.
Figure 3:
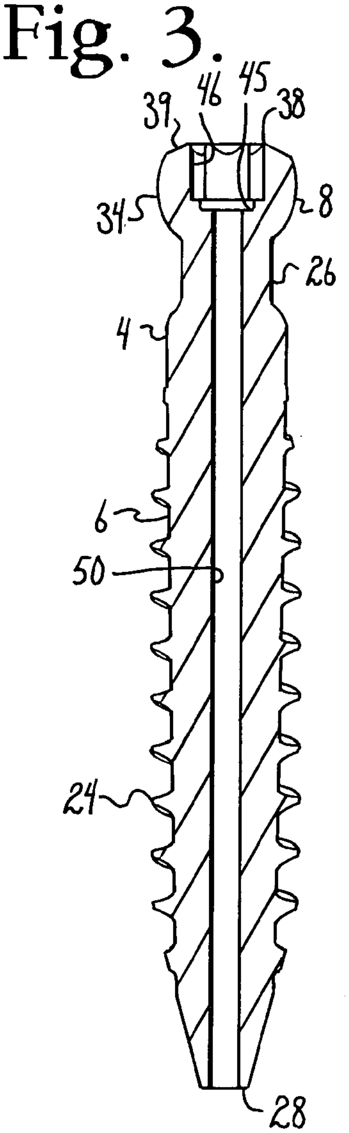
FIG. 3 is a reduced cross-sectional view taken along the line 3-3 of FIG. 2.
Figure 4:
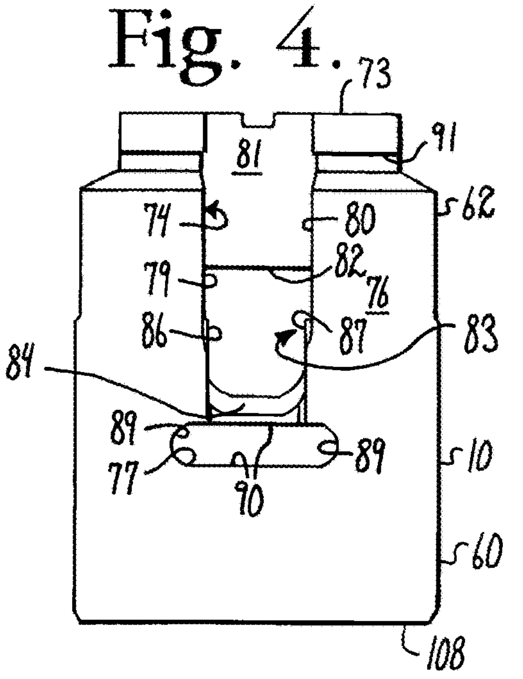
FIG. 4 is an enlarged side elevational view of the receiver of FIG. 1.
Figure 5:
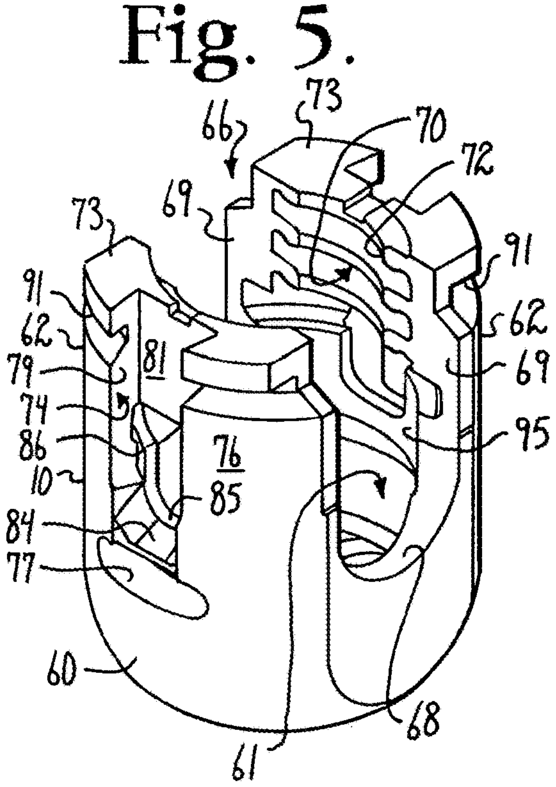
FIG. 5 is an enlarged perspective view of the receiver of FIG. 4.
Figure 6:
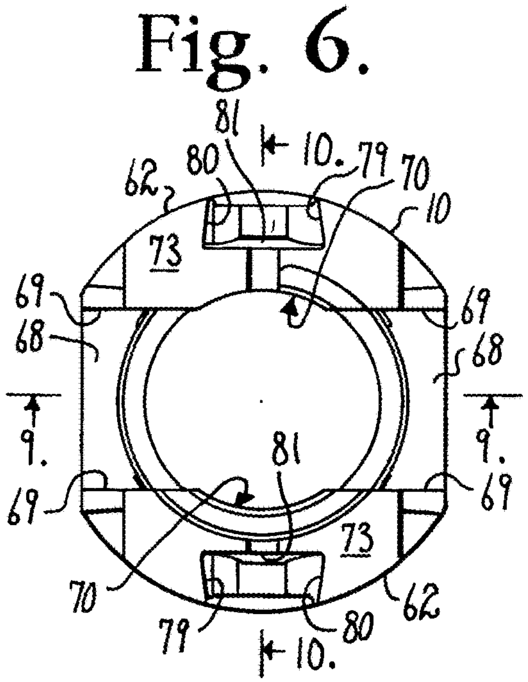
FIG. 6 is an enlarged top plan view of the receiver of FIG. 4.
Figure 7:
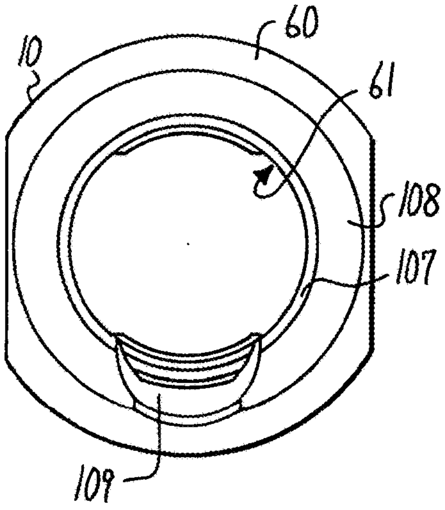
FIG. 7 is an enlarged bottom plan view of the receiver of FIG. 4.
Figure 11:
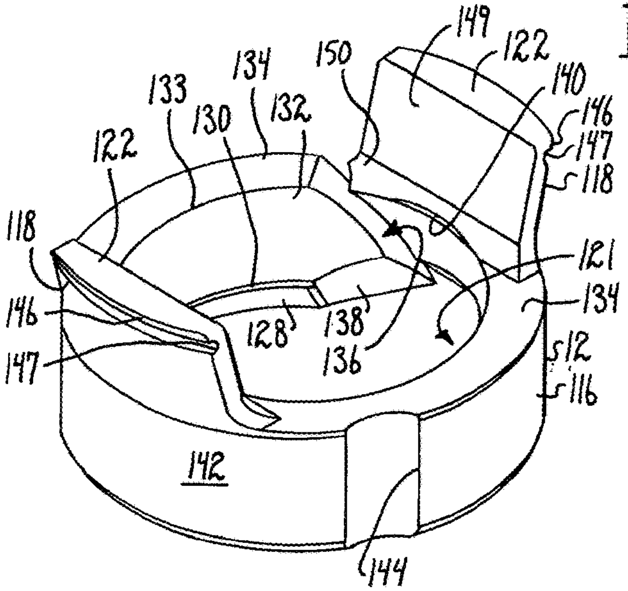
FIG. 11 is an enlarged perspective view of the retainer of FIG. 1.
Figure 12:
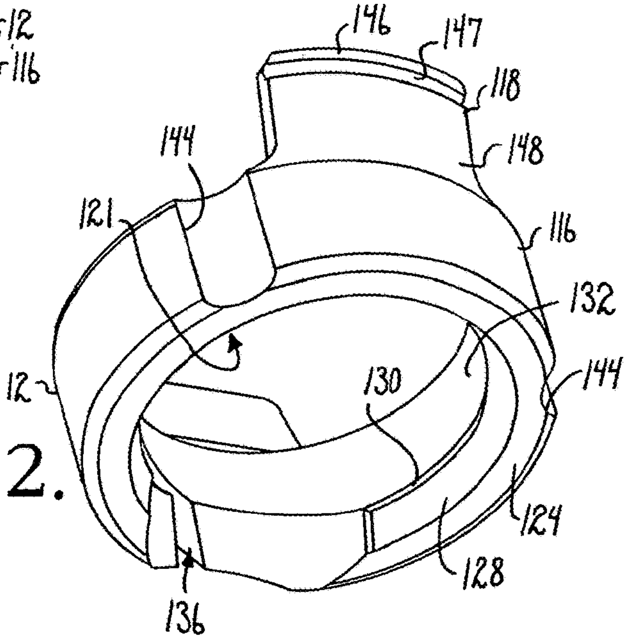
FIG. 12 is another perspective view of the retainer of FIG. 11.
Figure 13:
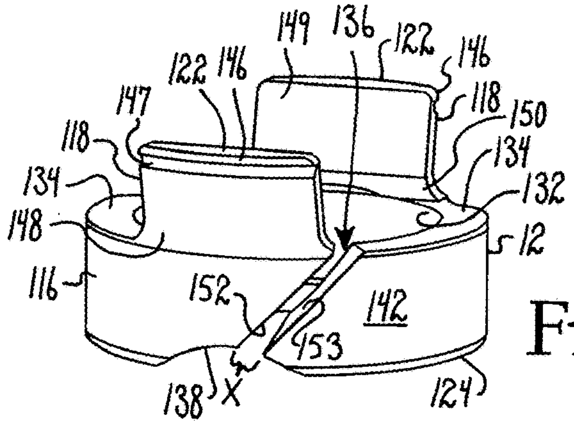
FIG. 13 is another reduced perspective view of the retainer of FIG. 11.
Figure 14:
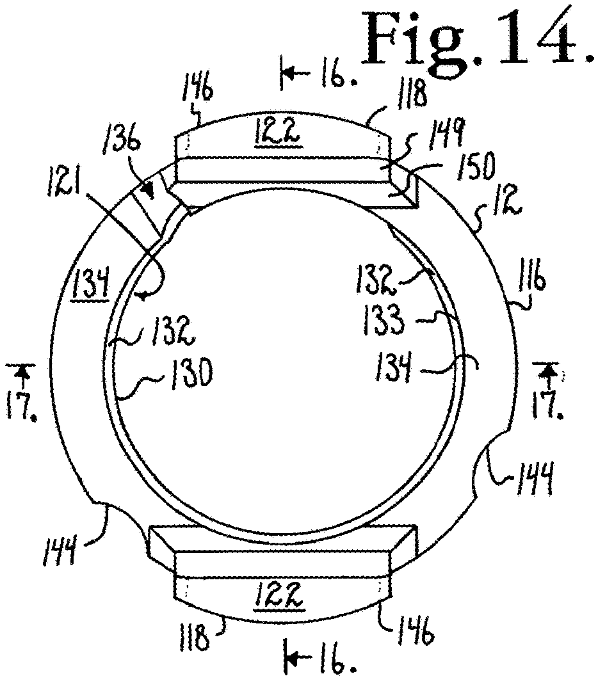
FIG. 14 is a top plan view of the retainer of FIG. 11.
Figure 15:
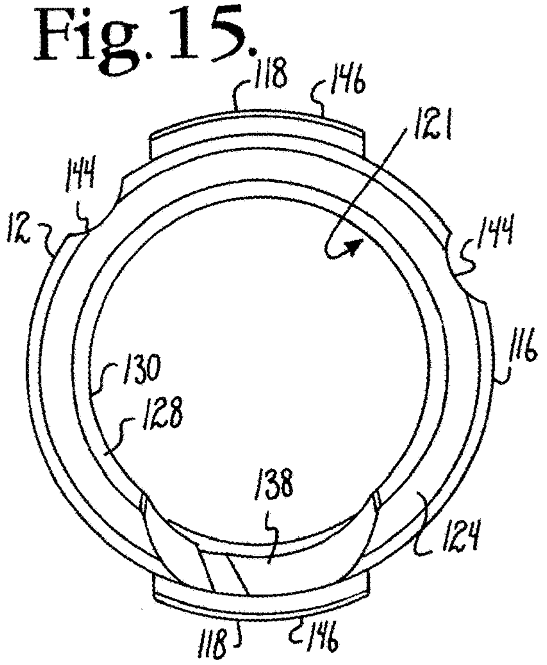
FIG. 15 is a bottom plan view of the retainer of FIG. 11.
Figure 16:
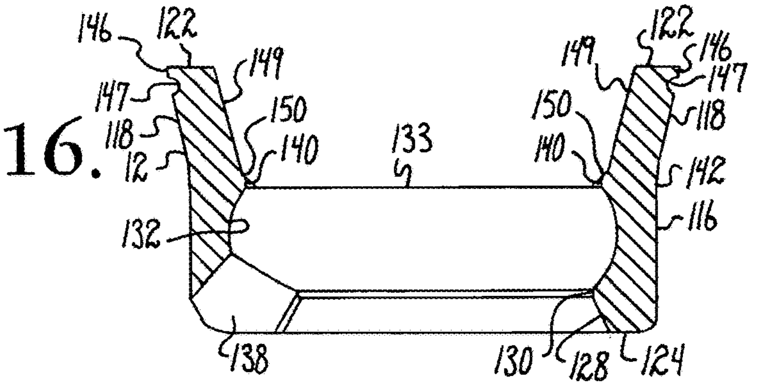
FIG. 16 is a cross-sectional view taken along the line 16-16 of FIG. 14.
Figure 17:
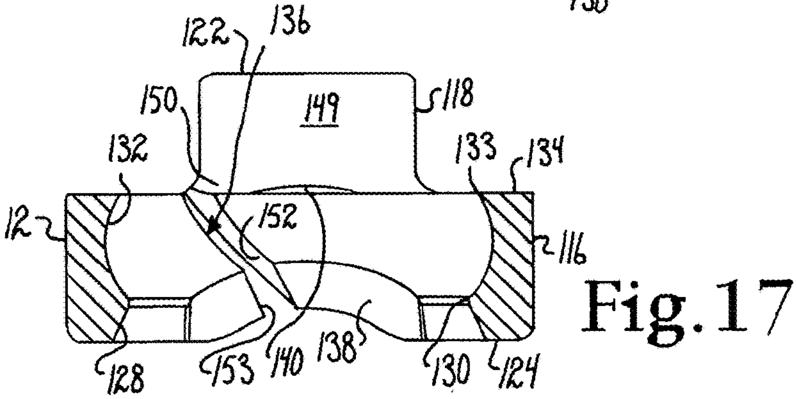
FIG. 17 is a cross-sectional view taken along the line 17-17 of FIG. 14.
Figure 18:
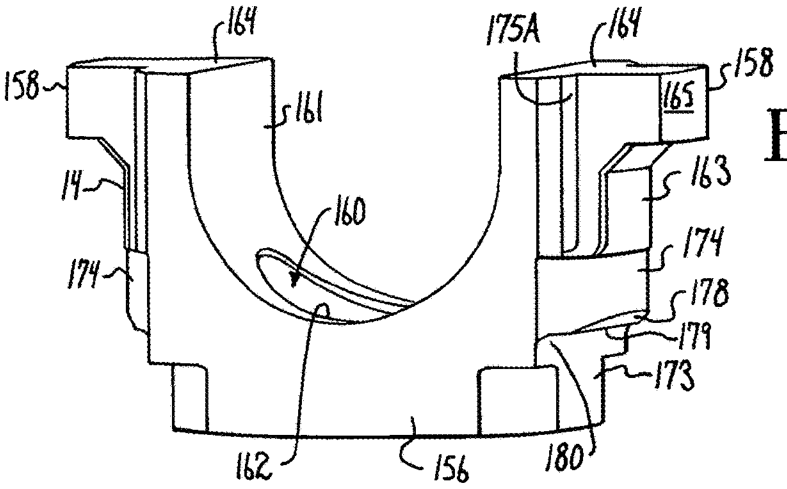
FIG. 18 is an enlarged perspective view of the insert of FIG. 1.
Figure 19:
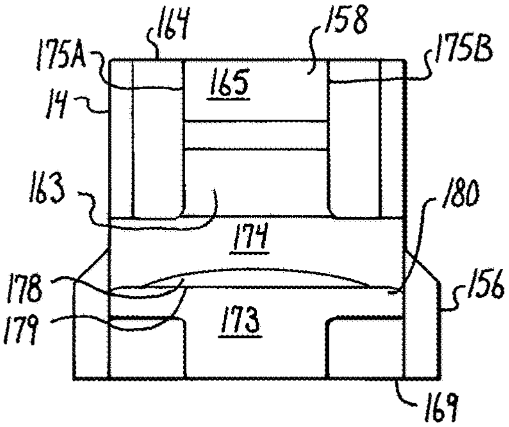
FIG. 19 is a side elevational view of the insert of FIG. 18.
Figure 20:
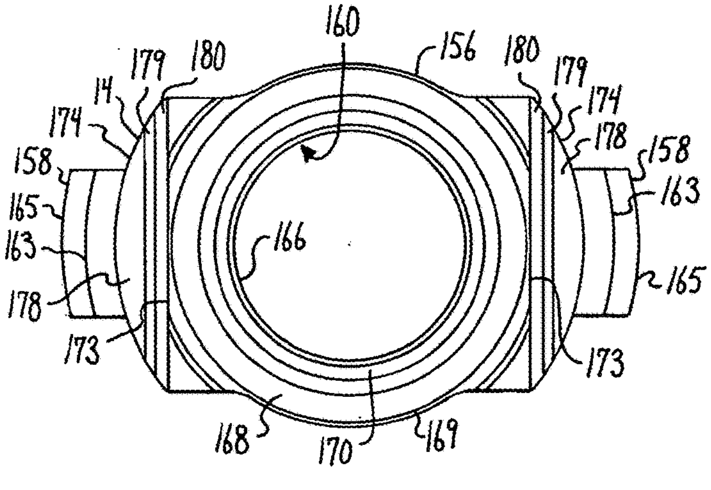
FIG. 20 is a bottom plan view of the insert of FIG. 18.
Figure 21:
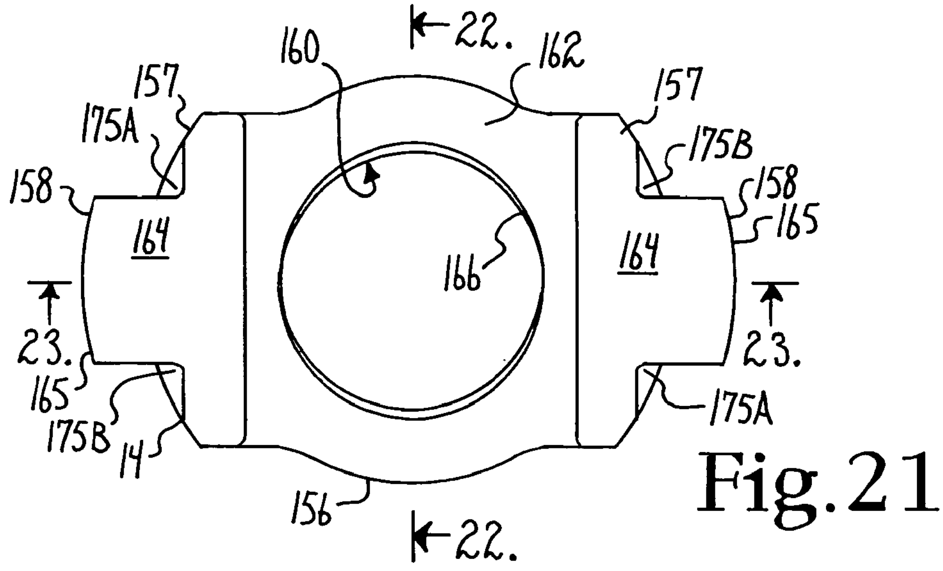
FIG. 21 is a top plan view of the insert of FIG. 18.
Figure 22:
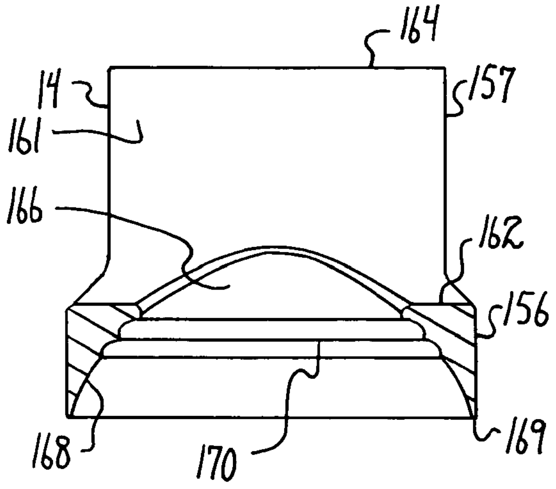
FIG. 22 is a cross-sectional view taken along the line 22-22 of FIG. 21.
Figure 23:
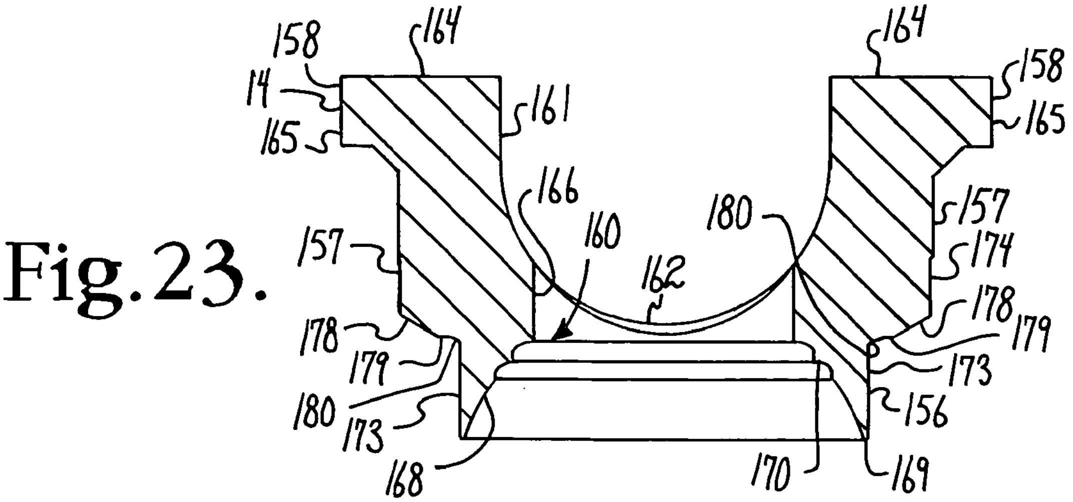
FIG. 23 is a cross-sectional view taken along the line 23-23 of FIG. 21.

The shank 4, best illustrated in FIGS. 1-3, is elongate, with the shank body 6 having a helically wound bone implantable thread 24 (single or dual lead thread form and different thread types) extending from near a neck 26 located adjacent to the upper portion or head 8, to a tip 28 of the body 6 and extending radially outwardly therefrom. During use, the body 6 utilizing the thread 24 for gripping and advancement is implanted into the vertebra 17 leading with the tip 28 and driven down into the vertebra with an installation or driving tool (not shown), so as to be implanted in the vertebra to a location at or near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion or head 8 that provides a connective or capture apparatus disposed at a distance from the upper end 32 and thus at a distance from the vertebra 17 when the body 6 is implanted in such vertebra.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 that in some embodiments terminates at a substantially planar top or rim surface 38. In the illustrated embodiment, a frusto-conical surface 39 extends from the spherical surface 34 inwardly to the top surface 38, providing additional clearance during pivoting of the shank with respect to the receiver 10 and the insert 14. The spherical surface 34 has an outer radius configured for temporary frictional, non-floppy, sliding cooperation with one or more edges or surfaces of the retainer 12, as well as ultimate frictional engagement with the insert 14 at an inner partially spherical surface thereof, as will be discussed more fully in the paragraphs below. The spherical surface 34 shown in the present embodiment is substantially smooth, but in some embodiments may include a roughening or other surface treatment and is sized and shaped for cooperation and ultimate frictional engagement with the compression insert 14 as well as ultimate frictional engagement with a lower ring-like portion of the retainer 12. The shank spherical surface 34 is locked into place exclusively by the insert 14 and the retainer 12 lower portion and not by inner surfaces defining the receiver cavity.

A counter sunk stepped or graduated annular seating surface or base 45 partially defines an internal drive feature or imprint 46. In some embodiments of the invention, the surface 45 is substantially planar. The illustrated internal drive feature 46 is an aperture formed in the top surface 38 and has a star shape designed to receive a tool (not shown) of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or a multi-lobular or hex-shaped aperture. The graduated seat or base surfaces 45 of the drive feature 46 are disposed substantially perpendicular to the axis A with the drive feature 46 otherwise being coaxial with the axis A. As illustrated in FIGS. 2 and 3, the drive seat 45 having beveled or stepped surfaces advantageously further enhances gripping with the driving tool. In operation, a driving tool (not shown) is received in the internal drive feature 46, being seated at the base 45 and engaging the faces of the drive feature 46 for both driving and rotating the shank body 6 into the vertebra 17, either before the shank 4 is attached to the receiver 10 or after the shank 4 is attached to the receiver 10, with the shank body 6 being driven into the vertebra 17 with the driving tool extending into the receiver 10.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper opening communicating with the external drive 46 at the driving seat 45. The bore 50 is coaxial with the threaded body 6 and the upper portion 8. The bore 50 provides a passage through the shank 4 interior for a length of wire (not shown) inserted into the vertebra 17 prior to the insertion of the shank body 6, the wire providing a guide for insertion of the shank body 6 into the vertebra 17. It is foreseen that the shank could be solid and made of different materials, including metal and non-metals.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$, tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-10, the receiver 10 has a generally U-shaped appearance with partially discontinuous and partially cylindrical inner and outer profiles. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 17, the axis B is typically disposed at an angle with respect to the axis A, as shown, for example, in FIGS. 41-46.

The receiver 10 includes a substantially cylindrical base 60 defining a bore or inner cavity, generally 61, the base 60 being integral with a pair of opposed upstanding arms 62 forming a cradle and defining a channel 64 between the arms 62 with an upper opening, generally 66, and a U-shaped lower channel portion or seat 68, the channel 64 having a width for operably snugly receiving the rod 21 or portion of another longitudinal connector between the arms 62, the channel 64 communicating with the base cavity 61. Inner opposed substantially planar arm surfaces 69 partially define the channel 64 directly above the seat 68 and are located on either side of each arm interior surface generally 70, that includes various inner cylindrical profiles, an upper one of which is a partial helically wound guide and advancement structure 72 located adjacent top surfaces 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-threadlike helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms 62 could have break-off extensions.

An opposed pair of vertically extending outer grooves, generally 74, running substantially parallel to the receiver axis B are centrally formed in outer cylindrical surfaces 76 of the arms 62. Each groove 74 runs centrally from the respective arm top surface 73 and terminates at a location spaced from a lower through aperture 77. Each aperture 77 extends through the respective arm surface 77 to the respective inner arm surface 70. Each aperture 77 is located near or adjacent the receiver base 60. A portion of each groove 74 also extends completely through the respective arm 62 and opens into the inner arm surface 70. Specifically, each groove 74 has an upper opening partially defined by a pair of opposed surfaces 79 and 80 and a substantially planar outer wall surface 81 extending between the surfaces 79 and 80. The planar wall surface terminates at the top surface 73 and at a lower surface 82. The lower surface 82 partially defines an open or through aperture portion 83 of each groove, the lower surface 82 extending between to the respective inner arm surface 70. The opposed surfaces 79 and 80 are disposed at an angle with respect to each other, forming the groove 74 as a dovetail-like space for easily receiving an elongate tool (not shown) that enters into the groove 74 at the arm top surface 73 and is kept in close sliding contact with the surface 81 by the orientation of the surfaces 79 and 80 angling toward one another with the tool sliding along the surface 81 and ultimately into contact with winged portions of the insert 14 that extend through the aperture 83 as will be described in greater detail below. At the through aperture 83, the dovetail surfaces 79 and 80 terminate at or near a generally u-shaped lower surface 84, the surface 84 also sloping downwardly and outwardly toward the outer arm surface 76 from a lower ledge 85 that partially defines the through aperture 83 at the respective arm inner surface 70. The ledge 85 is spaced from and located directly below the wall 81. Between the ledge 85 and the wall 81 and integral with each of the groove surfaces 79 and 80 are opposed crimping walls or flat tabs 86 and 87 that extend from the respective surfaces 79 and 80 at the inner arm surface 70 and are generally directed toward one another into the through aperture 83 space. The crimping walls or tabs 86 and 87 are sized and shaped for pressing or crimping some or all of the tab material into grooves of the insert 14 to prohibit rotation and misalignment of the insert 14 with respect to the receiver 10 as will be described in greater detail below. In other embodiments of the invention, other surfaces at or near the grooves 74 may be inwardly crimped. The illustrated through apertures 77 located below the grooves 74 are relatively narrow, each including a pair of opposed circular segments 89 extending outwardly from the nearby groove 74, the segments 89 being connected by upper and lower parallel walls, forming a generally rectangular portion 90. The through apertures 77 are sized and shaped for receiving spring tab portions of the retainer 12 during assembly and final operation that capture and retain the retainer 12 within the receiver as shown, for example, in FIG. 25. It is foreseen that in some embodiments of the invention, the apertures 77 will have an upper portion that is not a through-aperture, but rather a recessed wall of the receiver that allows for the spring tab portions to partially expand into contact with such a recessed wall, but remain slightly compressed to provide increased friction fit between the retainer and the shank head during manipulation of the shank with respect to the receiver. Then, during a final locking procedure, the spring tab portions will be further lowered to extend completely through a lower through aperture area of the respective aperture 77.

The receiver 10 is a one-piece or integral structure and is devoid of any spring tabs or collet-like structures. Preferably the insert and/or receiver are configured with structure for blocking rotation of the insert with respect to the receiver, such as the crimp walls 86 and 87, but allowing some up and down movement of the insert with respect to the receiver during the assembly and implant procedure. Also formed in each outer arm surface 76 near the top surface 73 is an undercut tool receiving and engaging groove 91. Some or all of the apertures and grooves described herein, including, but not limited to grooves 74, apertures 83, and grooves 91 may be used for holding the receiver 10 during assembly with the insert 14, the retainer 12 and the shank 4; during the implantation of the shank body 6 into a vertebra when the shank is pre-assembled with the receiver 10; during assembly of the bone anchor assembly 1 with the rod 21 and the closure structure 18; and during lock and release adjustment of alternative inserts according to the invention with respect to the receiver 10, either into or out of frictional engagement with the inner surfaces of the receiver 10 as will be described in greater detail below. It is foreseen that tool receiving grooves or apertures may be configured in a variety of shapes and sizes and be disposed at other locations on the receiver arm 62 outer surfaces 76 and/or inner surfaces 70 as well as the base 60 outer or inner surfaces.

Returning to the interior surface 70 of the receiver arms 62, located below the guide and advancement structure 72 is a discontinuous cylindrical surface 92 partially defining a run-out feature for the guide and advancement structure 72. The cylindrical surface 92 is sized and shaped to receive an upper winged portion of the insert 14 as will be described in greater detail below. Therefore, the surface 92 has a diameter greater than a greater diameter of the guide and advancement structure 72. The illustrated receiver 10 further includes sloped, stepped or chamfered surfaces above and below the surface 92. The surface 92 is divided not only by the U-shaped channel 64, but also by each of the through apertures 83, resulting in the surface 92 being in four sections. A lower partially sloping or stepped ledge 94 at the base of the cylindrical surface 92 slopes downwardly toward the receiver base 60 and then extends inwardly toward the axis B, the surface 94 terminating at a discontinuous cylindrical surface 95. A discontinuous inwardly sloping surface or narrow ledge 96 is located below the surface 95 and is adjacent another partially discontinuous cylindrical surface 97. It is noted that in some embodiments of the invention, the surfaces 95 and 97 are combined and form a single cylindrical surface. The through aperture 83 extends through the surface 95 while the through aperture 77 extends through the surface 97. In the illustrated embodiment, the aperture 77 is located and sized so that the sloping surface 96 and a portion of the cylindrical surface 97 form a narrow inwardly facing projection or lip for temporary engagement with grooves formed in outwardly extending resilient spring tabs of the retainer 12 as will be described in greater detail below. Portions of the surfaces 95 are pressed into engagement with the insert 14 when the thin, deformable walls or tabs 86 and 87 are pressed toward the insert 14 as will be described in greater detail below. A lower portion of the surface 97 located between the arms 62 and below the U-shaped channel seating surface 68 terminates at a discontinuous annular surface or ledge 98 disposed substantially perpendicular to the axis B, but could be oblique. The discontinuous surface 98 partially defines the base cavity 61. The surface 98 terminates at each of the through apertures 77. A continuous cylindrical surface 99 is located below and adjacent to the surface 98 and the apertures 77. The cylindrical surface 99 is oriented substantially parallel to the axis B and is sized and shaped to receive an expanded portion of retainer 12. The surface 99 defines a circumferential recess that is sized and shaped to receive the retainer 12 as it expands around the shank upper portion 8 as the shank 8 moves upwardly toward the channel 64 during assembly. It is foreseen that the recess could be tapered or conical in configuration. A cylindrical surface 101 located below the cylindrical surface 99 is sized and shaped to closely receive and surround a lower portion of the retainer 12 when the retainer is in a reduced deployment position as shown in FIG. 39, for example. Thus, the cylindrical surface 101 has a diameter smaller than the diameter of the cylindrical surface 99 that defines the expansion area or expansion chamber for the retainer 12. The surface 101 is joined or connected to the surface 99 by one or more beveled, curved or conical surfaces 102. The surfaces 102 allow for sliding and nominal or deployment positioning of the retainer 12 into the space defined by the surface 101 and ultimate seating of the retainer 12 on a lower substantially horizontal annular surface 104 located below and adjacent to the cylindrical surface 101. The surface 104 is oriented substantially perpendicular to the axis B.

Figure 44:
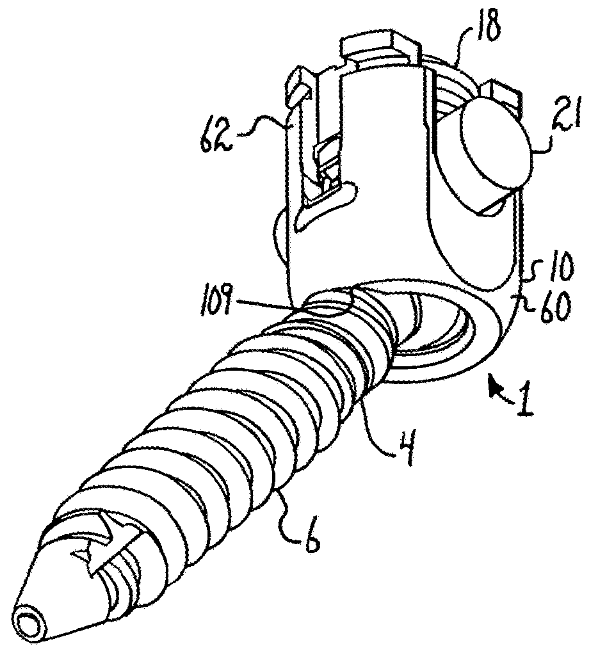
FIG. 44 is a reduced and partial perspective view of the assembly of FIG. 40, but with the shank shown disposed at about a forty degree (medial) angle with respect to the receiver.
Figure 45:
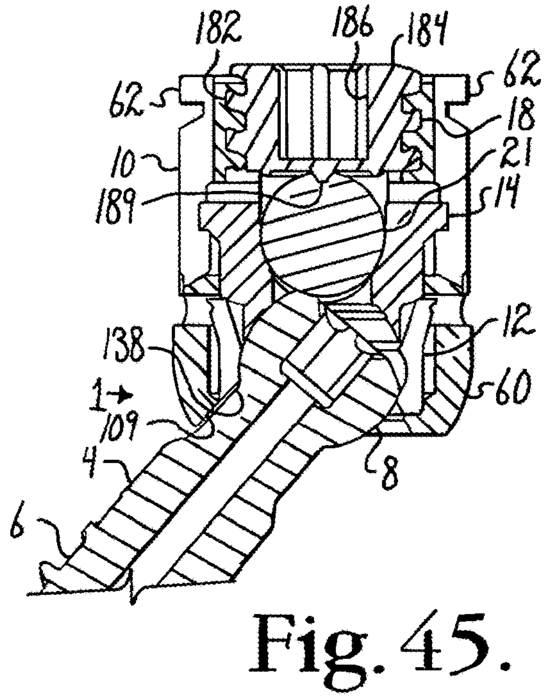
FIG. 45 is a partial front elevational view of the assembly as shown in FIG. 44 with portions broken away to show the detail thereof.

Located below and adjacent to the annular seating surface 104 is another substantially cylindrical surface 106 that communicates with a beveled or flared bottom opening surface 107, the surface 107 communicating with an exterior base surface 108 of the base 60, defining a lower opening, generally 110, into the base cavity 61 of the receiver 10. Formed in a portion of the base surface 108, as well as in portions of the surfaces 107, 106, 104 and 101 is a curvate cut-out or cupped surface 109 located substantially centrally and directly below one of the arms 62. As illustrated in FIGS. 44 and 45, for example, the cupped surface 109 is sized and shaped for providing clearance for an increased angle of articulation between the shank 4 and the receiver 10 as will be described in greater detail below.

With particular reference to FIGS. 1 and 11-17, the lower open or split friction fit retainer 12, that operates to capture the shank upper portion 8 within the receiver 10, has a central axis that is operationally the same as the axis B associated with the receiver 10 when the shank upper portion 8 and the retainer 12 are installed within the receiver 10. The retainer 12 includes a substantially cylindrical discontinuous body 116. Extending upwardly and outwardly from the body 116, and integral thereto, are a pair of opposed spring arms or tabs 118. The retainer ring 12 is made from a resilient material, such as a stainless steel or titanium alloy, so that the retainer 12 body 116 may be expanded and the tabs 118 of the retainer may be manipulated during various steps of assembly as will be described in greater detail below. The retainer 12 has a central channel or hollow through bore, generally 121, that passes entirely through the retainer 12 from tab 118 top surfaces 122 to a bottom surface 124 of the retainer body 116. Surfaces that define the channel or bore 121 at the body 116 include an inner lower frusto-conical surface 128 adjacent to the retainer body bottom surface 124, a narrow substantially cylindrical surface 130 adjacent the frusto-conical surface 128 and a discontinuous concave radiused or partially spherical surface 132 located adjacent the cylindrical surface 130, the surface 132 extending upwardly to an upper discontinuous edge or rim surface 133 located between the spring tabs 118, each rim surface 133 partially defined by a retainer body upper or top surface 134, the top surface being substantially planar and discontinuous, disposed substantially parallel to the body bottom surface 124 and terminating at each of the spring tabs 118 and at a slit, generally 136. The obtuse slit 136 creates a split or open ring retainer 12, the slit cutting entirely through the retainer body 116. In some embodiments, such a slit may run perpendicular to the surfaces 124 and 134. The slit 136 is for expansion purposes only during pop-on or snap-on assembly with the shank head 8. The retainer 12 base does not necessarily need to be contracted when loaded into the receiver 10, while the spring tabs 118 can be. The illustrated inner radiused or partially spherical surface 132 has a radius that is smaller than the radius of the spherical shank surface 34. The slit 136 is disposed at an obtuse angle with respect to the top surface 134 and extends between the top surface 134 and a concave cut-out or cupped surface 138 formed in the body bottom surface 124. The slit can be of different shapes and located in other locations. At each of the spring tabs 118, the rim or edge 132 widens to form a narrow inner partial cylindrical surface 140. It is foreseen that in other embodiments of the invention, the surface 140 may be radiused or otherwise curved, convex or concave. The discontinuous surfaces 130, 133 and 140 are sized to advantageously frictionally engage the bone screw shank upper portion or head 8, allowing for an un-locked friction fit, non-floppy placement of the angle of the shank 4 with respect to the receiver 10 during surgery prior to locking of the shank 4 with respect to the receiver 10 near the end of the procedure. In the locked position, depending upon the angular orientation of the shank head 8, the surfaces and or edges 133 do not substantially engage the shank head 8. The discontinuous cupped surface 138 that is located on either side of the slit 136 and is substantially formed in the bottom surface 124, the frusto-conical surface 128 and the inner concave radiused surface 132, is positioned, sized and shaped to eventually cooperate with the cupped surface 109 of the receiver 10, allowing for an increased angular orientation of the shank 4 with respect to the receiver 10 as will be described in greater detail below.

The retainer body 116 has an outer substantially cylindrical profile defined by an outer cylindrical surface 142 sized and shaped to closely and slidingly fit within the receiver cavity 61. Formed in the surface 142 is one or more vertically extending grooves 144, the illustrated embodiment has two grooves 144. As will be described with respect to FIGS. 47-54, more or fewer grooves at inner as well as outer surfaces of the retainer are shown in alternative embodiments of the retainer 12.

The opposed pair of spring tabs 118 extend outwardly away from one another and thus outwardly from the body 116 outer cylindrical surface 142. Each spring tab 118 is sized and shaped to closely cooperate and frictionally engage surfaces of the receiver 10 and the through bore 77 as will be described in greater detail below. An outer surface 146 of each spring tab 118 located adjacent each upper surface 122 as well as an optional substantially horizontal elongate notch or grooved surface 147 are sized and shaped to cooperate with and frictionally engage the receiver inner arm surfaces, as shown, for example, in FIG. 35. The outer surface 146 extends downwardly below the notched surface 147 to a location at or near the body outer cylindrical surface 142. In the illustrated embodiment, an outer transition surface 148 spans between the surface 146 and the surface 142. The notches 147 (which in some embodiments may be replaced by projections, multiple grooves or notches of various geometries and orientations, for example), aid to resiliently hold the retainer in an upper portion of the receiver cavity 61 when desired, but also resiliently release when the retainer 12 is pressed into a lower portion of the receiver cavity 61. The illustrated spring tabs 118 each include one or more planar (as illustrated) or curved concave inner surfaces 149 running from the top surface 122 to a tab base seat, surface or surfaces 150 located adjacent to the cylindrical inner surface 146 as well as the body top surfaces 134. The surfaces 149 extend both outwardly and upwardly from the base seat surfaces 150. It is foreseen that in other embodiments of the invention, fewer or greater number of planar or other surfaces with other geometries may extend between the top surface 122 and the inner surfaces defining the body 116 of the retainer 12.

The through slit 136 of the resilient retainer 12 is defined by first and second end surfaces, 152 and 153 disposed in spaced relation to one another (they may also be touching) when the retainer is in a neutral or nominal state. Both end surfaces 152 and 153 are disposed at an angle with respect to the bottom surface 124. A width X between the surfaces 152 and 153 is very narrow (slit may be made by EDM process) to provide stability to the retainer 12 during operation. Because the retainer 12 is top loadable in a neutral state and the retainer 12 does not need to be compressed to fit within the receiver cavity 61 at the cylindrical surface 99; the width X may be much smaller than might be required for a bottom loaded compressible retainer ring. The initial gap X of the retainer 12 prior to attachment to the shank head 8 functions only in expansion to allow the retainer 12 to expand about the shank head 8. This results in a stronger retainer that provides more surface contact with the shank upper portion 8 upon locking, resulting in a sturdier connection with less likelihood of failure than a retainer ring having a greater gap. Furthermore, because the retainer 12 body 116 is only expanded and never compressed inwardly beyond the initial neutral state prior to assembly, the retainer 12 does not undergo the mechanical stress that typically is placed on spring ring type retainers known in the prior art that are both compressed inwardly and expanded outwardly during assembly. It has been found that once the retainer 12 is expanded about the shank head 8, the retainer 12 may return to a new nominal or neutral orientation in which a gap between the surfaces 152 and 153 is slightly greater than the gap X. As will be described in greater detail below, the assembly 1 advantageously provides for access to the insert 14 and the retainer 12 to allow for pressing of the retainer 12 down onto the receiver seat portion 104 and reducing the retainer 12 into the receiver 10 inner cylindrical surface 101 as desired, prior to locking of the assembly 1 with a rod and closure top.

With particular reference to FIGS. 1 and 18-23, the compression insert 14 is illustrated that is sized and shaped to be received by and down-loaded into the receiver 10 at the upper opening 66. The compression insert 14 has an operational central axis that is the same as the central axis B of the receiver 10. In operation, the insert advantageously frictionally engages the bone screw shank upper portion 8. As will be described in greater detail below with respect to the alternative insert 214 shown in FIGS. 55-58, in some embodiments of the invention, the insert that has locked the shank 4 in a desired angular position with respect to the receiver 10, by, for example, compression from the rod 21 and closure top 18, is also forced into an interference fit engagement with the receiver 10 at an outer surface thereof and thus is capable of retaining the shank 6 in a locked position even if the rod 21 and closure top 18 are removed. Such locked position may also be released by the surgeon if desired. The non-locking insert 14 as well as the locking insert 214 are preferably made from a solid resilient material, such as a stainless steel or titanium alloy, so that portions of the insert may be pinched or pressed, if necessary, and un-wedged from the receiver 10 with a release tool.

The non-locking compression insert 14 includes a substantially cylindrical body 156 integral with a pair of upstanding arms 157. Extending outwardly from each arm 157 is an integral wing or extension 158. A bore, generally 160, is disposed primarily within and through the body 156 and communicates with a generally U-shaped through channel formed by a saddle 161 that is substantially defined by the upstanding arms 157. The saddle 161 has a lower seat 162 sized and shaped to closely, snugly engage the rod 21. It is foreseen that an alternative embodiment may be configured to include planar holding surfaces that closely hold a square or rectangular bar as well as hold a cylindrical rod-shaped, cord, or sleeved cord longitudinal connecting member. The arms 157 disposed on either side of the channel extend upwardly and outwardly from the body 156 and terminate at top surfaces 164. The arms 157 are sized and configured for ultimate placement beneath the cylindrical run-out surface 92 located below the receiver guide and advancement structure 72 with the wings 158 extending through the receiver aperture 83 located below the arm surface 82. It is foreseen that in some embodiments of the invention, the arms may be extended upwardly and the closure top configured such that the arms and, more specifically, the surfaces 164 ultimately directly engage the closure top 18 for locking of the polyaxial mechanism, for example, when the rod 21 is made from a deformable material. In such embodiments, the insert 14 would include a rotation blocking structure or feature that abuts against cooperating structure located on an inner wall of the receiver 10, preventing rotation of the insert with respect to the receiver when the closure top is rotated into engagement with the insert. In the present embodiment, the arms 157 include upper outer cylindrical surfaces 163 located below the wings 158 and the top surfaces 164, the surfaces 163 located within the receiver arm cylindrical surfaces 95 and the top surfaces 164 being ultimately positioned in spaced relation with the closure top 18, so that the closure top 18 frictionally engages the rod 21 only, pressing the rod 21 downwardly against the seating surface 162, the insert 14 in turn pressing against the shank 4 upper portion 8 that presses against the retainer 12 to lock the polyaxial mechanism of the bone screw assembly 1 at a desired angle. The wings 158 are partially defined by the upper surfaces 164 and partially defined by outer partially cylindrical surfaces 165. The surfaces 165 are sized and shaped for rotation within the receiver arm cylindrical surfaces 92 during assembly of the insert 14 with the receiver 10 as will be described in greater detail below.

The bore, generally 160, is substantially defined at the body 156 by an inner cylindrical surface 166 that communicates with the seat 162 and a lower concave substantially spherical surface 168 having a radius the same or substantially similar to a radius of the surface 34 of the shank upper portion 8. The surface 168 terminates at an annular edge or rim base surface 169 of the body 156. Located between the cylindrical surface 166 and the spherical surface 168 or located along the spherical surface 168 is a shank gripping surface portion, generally 170. The gripping surface portion 170 includes one or more stepped surfaces or ridges sized and shaped to grip and penetrate into the shank head 8 when the insert 14 is locked against the head surface 34. It is foreseen that the stepped surface portion 170 may include greater or fewer number of stepped surfaces. It is foreseen that the shank gripping surface portion 170 and also the spherical surface 168 may additionally or alternatively include a roughened or textured surface or surface finish, or may be scored, knurled, or the like, for enhancing frictional engagement with the shank upper portion 8.

The compression insert 14 through bore 160 is sized and shaped to receive the driving tool (not shown) therethrough that engages the shank drive feature 46 when the shank body 6 is driven into bone with the receiver 10 attached. Also, in some locking embodiments of the invention, the bore receives a manipulation tool (not shown) used for releasing the insert from a locked position with the receiver, the tool pressing down on the shank and also gripping the insert at through bores located in the arms or with other tool engaging features. For example, a manipulation tool for releasing the insert from the receiver 10 may also access such bores from the receiver through the apertures in the receiver. Thereby, tools can be configured to release a locking insert from the inside and outside of the receiver 10.

The illustrated insert 14 further includes a lower, planar outer arm surface 173 adjacent to the bottom rim 169 and an outer middle arm surface 174 located between the arm surface 164 and the lower surface 173. The surface 174 is recessed from the surface 164 and the surface 173 is recessed from the surface 174, giving the insert 14 arms an inwardly and downwardly stepped profile running from the top surfaces 164 to the bottom rim surface 169. The surface 174 is cylindrical, but in some embodiments may be planar or of another curved shape. Located at either side of the wings 158 and the arm surfaces 163 are vertically extending grooves or squared-off surface portions or notches 175A and 175B that run from the respective top surface 164 to the respective lower arm surface 174. The grooves 175A and 175B cooperate with the receiver crimp walls 86 and 87 to aid in alignment of the insert channel or saddle 161 with the receiver channel 64. Spanning between each arm surface 174 and each arm surface 173 is a sloping surface 178 that forms a ledge for cooperation with the retainer spring tabs 118, the surface 178 forming an oblique angle with the insert central axis. In some embodiments of the invention, the entire ledge is substantially perpendicular to the central axis of the insert 14. In the illustrated embodiment, the sloping outer ledge surface 178 is integral with an inner surface 179 that is substantially perpendicular to the central axis of the insert 14, the surface 179 located near or adjacent the arm surface 173. In the illustrated embodiment and curved transition surface 180 provides a rounded off corner connection between the surface 179 and the arm surface 173. The surfaces 179 abut against the retainer 12 spring tab top surfaces 122 during some of the early stages of assembly between the insert 14, the retainer 12 and the receiver 10, while the surfaces 178 provide adequate clearance for the retainer spring tabs 118 during later stages of assembly as will be described in greater detail below. Each of the arms 157 and the insert body 156 may include more surface features, such as cut-outs notches, bevels, etc. to provide adequate clearance for inserting the insert 14 into the receiver and cooperating with the retainer 12 during the different assembly steps as will be described in greater detail below.

The insert body 156 has an outer diameter slightly smaller than a diameter between crests of the guide and advancement structure 72 of the receiver 10, allowing for top loading of the compression insert 14 into the receiver opening 66, with the arms 157 of the insert 14 being located between the receiver arms 62 during insertion of the insert 14 into the receiver 10. Once the arms 157 of the insert 14 are generally located beneath the guide and advancement structure 72, the insert 14 is rotated in a clockwise direction into place about the receiver axis B until the wings 158 are located in the apertures 83 as will be described in greater detail below.

With reference to FIGS. 1 and 39-46, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys, non-metals and deformable and less compressible plastics, including, but not limited to rods made of elastomeric, polyetheretherketone (PEEK) and other types of materials, such as polycarbonate urethanes (PCU) and polyethelenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 39-40, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes a an outer helically wound guide and advancement structure 182 in the form of a flange that operably joins with the guide and advancement structure 72 disposed on the arms 62 of the receiver 10. The flange form utilized in accordance with the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 10 that may more advantageously engage longitudinal connecting member components. The illustrated closure structure 18 also includes a top surface 184 with an internal drive 186 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 186 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 188 of the closure is planar and further includes a point 189 and a rim 190 for engagement and penetration into the surface 22 of the rod 21 in certain embodiments of the invention. It is noted that in some embodiments, the closure top bottom surface 188 does not include the point and/or the rim. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62. An alternative closure top (not shown) for use with a deformable rod, such as a PEEK rod, for example, may include a domed lower surface in lieu of the point and rim surface of the closure top 18.

The assembly 1 receiver 10, retainer 12 and compression insert 14 are typically assembled at a factory setting that includes tooling for holding and alignment of the component pieces and pinching or compressing of the retainer 12 spring tabs 118 and rotating and otherwise manipulating the insert 14 arms, as well as crimping a portion of the receiver 10 toward the insert 14. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to preassemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost and improving logistics and distribution.

Pre-assembly of the receiver 10, retainer 12 and compression insert 14 is shown in FIGS. 24-31. With particular reference to FIG. 24, first the retainer 12 is inserted into the upper receiver opening 66, leading with one of the spring tabs 118 with both of the spring tab top surfaces 122 facing one arm 62 and the retainer bottom surface 124 facing the opposing arm 62 (shown in phantom). The retainer 12 is then lowered in such sideways manner into the channel 64 and partially into the receiver cavity 61, followed by tilting the retainer 12 such that the top surface 122 and thereafter the top surface 122 of the leading spring tab 118 is temporarily moved into a nearby receiver arm aperture 83. With reference to FIG. 25, the retainer 12 is then further tilted or turned and then manipulated downwardly within the receiver as shown in phantom, the spring tabs 118 being compressed inwardly as the retainer is lowered to a position within the cavity as shown in solid lines in FIG. 25, the retainer 12 bottom surface 124 ultimately seating on the receiver surface 104 and the spring tabs 118 returning to a neutral state, extending into the apertures 77. To accomplish the tilting and turning of the retainer 12 required for ultimately seating the retainer on the receive surface 104, the spring tab arm 118 may require some downward and upward tilting, shifting in and out of the aperture 83 until the tabs are pressed resiliently inwardly towards one another at the receiver surface 97 and finally allowed to spring outwardly at the apertures 77. At this time, the retainer 12 is captured within the receiver base cavity 61 unless the spring tabs 118 are squeezed toward one another so as to clear the through apertures 77.

With reference to FIGS. 25-27, the compression insert 14 is then downloaded into the receiver 10 through the upper opening 66 with the bottom surface 169 facing the receiver arm top surfaces 73 and the insert arm wings 158 located between the opposed receiver arms 62. The insert 14 is then lowered toward the receiver base 60 until the insert 14 arm upper surfaces 164 are adjacent the run-out area below the guide and advancement structure 72 defined in part by the cylindrical surface 92. Thereafter, the insert 14 is rotated (see the arrow K in FIG. 27) about the receiver axis B until the upper arm surfaces 164 are directly below the guide and advancement structure 72 and the insert wings 158 are extending through the receiver grooves 75 and into the apertures 83 located below the receiver surfaces 82 as illustrated in FIGS. 28-30 with the U-shaped channel 161 of the insert 14 aligned with the U-shaped channel 64 of the receiver 10. In some embodiments, the insert arms 157 may need to be compressed slightly during rotation to clear some of the inner surfaces 70 of the receiver arms 62. With particular reference to FIGS. 28 and 29, thereafter, the four receiver crimping walls or tabs 86 and 87 are then pressed inwardly toward and against the respective insert 14 v-notch or grooved surfaces 175A and 175B. The crimping walls 86 and 87 help retain the desired alignment between the insert 14 and the receiver 10 and prohibit relative rotation between the two parts. However, relative vertical movement between the insert 14 and the receiver 10 is possible as the crimping walls do not vertically fix the insert with respect to the receiver.

With particular reference to FIG. 30, a tool (not shown) is then used to grip the retainer spring tab arms 118 at outer surfaces 146, 148 thereof and squeeze or press the tabs 118 toward one another while moving the retainer 12 in an upward direction away from the surface 104 and near or into engagement with the insert 14 at the surface 179. When the spring tab surfaces 146 and outer grooves 147 are located within the receiver cylindrical surfaces 95 and 97, the manipulation tool (not shown) is released and the retainer grooves 147 engage the surfaces 97 located directly below the sloping ledge 96 as shown in FIG. 31. The resilient spring tabs 118 press against the surfaces 97, the portion of the surfaces 97 now disposed within the retainer grooves 147 prohibiting downward and upward movement of the retainer 12 within the receiver 10. The retainer 12 and the insert 14 are now in a desired position for shipping as an assembly along with the separate shank 4. The insert 14 is also fully captured within the receiver 10 by the guide and advancement structure 72 prohibiting movement of the insert 14 up and out through the receiver opening 66 as well as by retainer 12 located below the insert.

Typically, the receiver and retainer combination are shipped or otherwise provided to the end user with the spring tabs 118 wedged against the receiver as shown in FIG. 31. The receiver 10, retainer 12 and insert 14 combination is now pre-assembled and ready for assembly with the shank 4 either at the factory, by surgery staff prior to implantation, or directly upon an implanted shank 4 as will be described herein.

Figure 32:
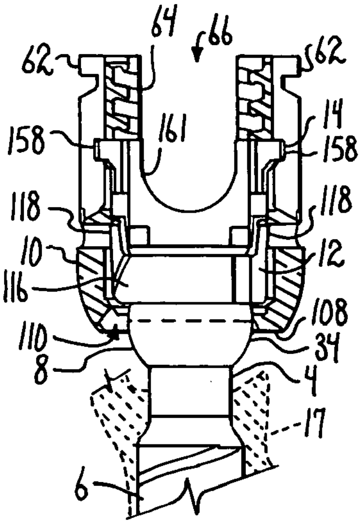
FIG. 32 is a reduced front elevational view with portions broken away, similar to FIG. 31, and further showing the shank of FIG. 1 in partial front elevation, the shank being in a first stage of assembly with the receiver and retainer, a hemisphere of the shank head and a vertebra portion are both shown in phantom.

As illustrated in FIG. 32, the bone screw shank 4 or an entire assembly 1 made up of the assembled shank 4, receiver 10, retainer 12 and compression insert 14, is screwed into a bone, such as the vertebra 17 (shown in phantom), by rotation of the shank 4 using a suitable driving tool (not shown) that operably drives and rotates the shank body 6 by engagement thereof at the internal drive 46. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires and attachable tower tools mating with the receiver. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

Figure 33:
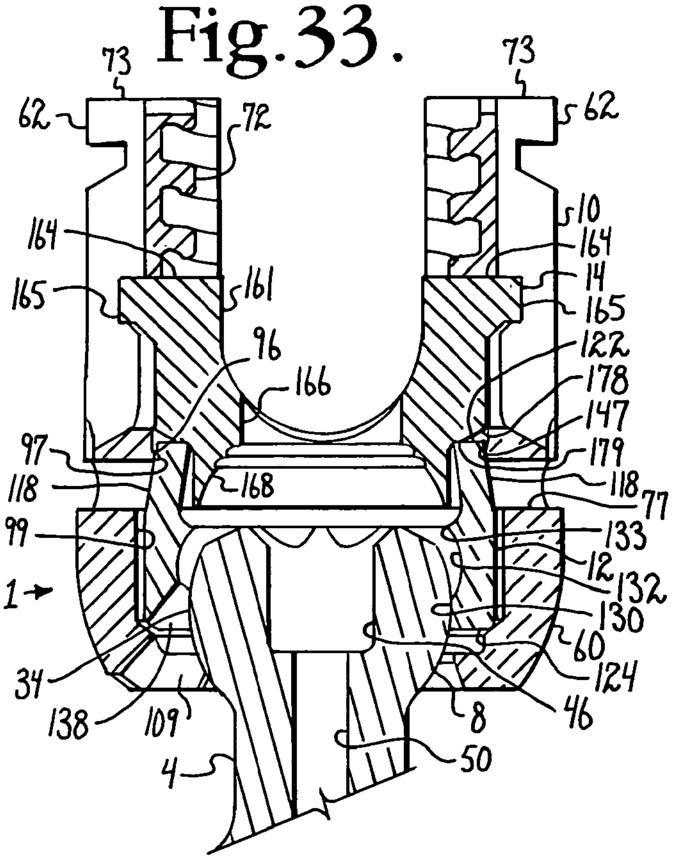
FIG. 33 is an enlarged and partial front elevational view with portions broken away, similar to FIG. 32, showing the retainer lower portion in an expanded state about a mid-portion of the shank head.
Figure 34:
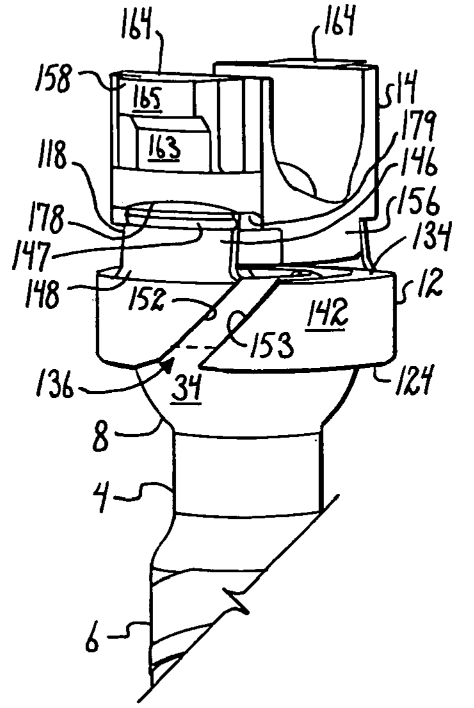
FIG. 34 is a reduced and partial perspective view (the receiver being completely removed) of the assembly as shown in FIG. 33.
Figure 35:
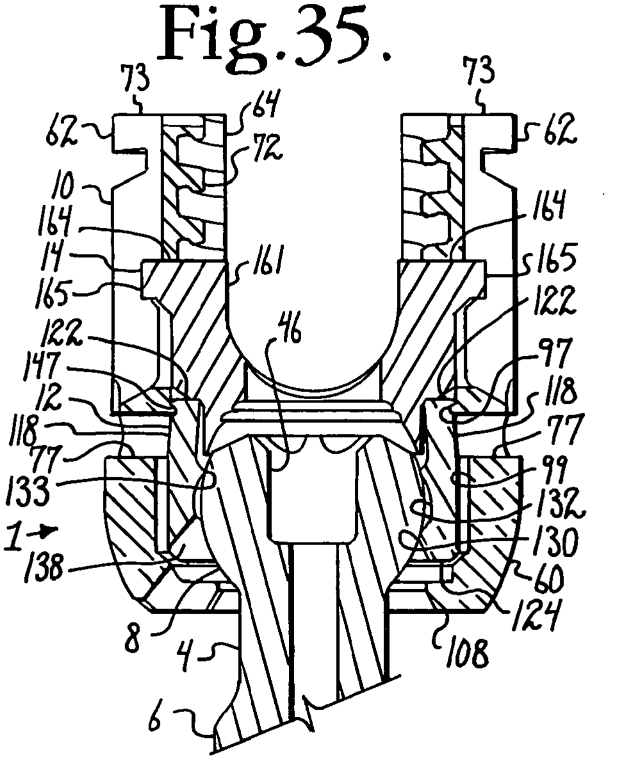
FIG. 35 is a reduced and partial front elevational view with portions broken away, similar to FIG. 33, the spherical shank upper portion or head shown fully captured by the retainer.

With further reference to FIG. 32, the pre-assembled receiver, insert and retainer are placed above the shank upper portion 8 until the shank upper portion is received within the opening 110. With particular reference to FIGS. 32-35, as the shank upper portion 8 is moved into the interior 61 of the receiver base, the shank upper portion 8 presses upwardly against the retainer 12 in the receiver recess partially defined by the cylindrical surface 99. As the shank head 8 continues to move upwardly toward the channel 64, the shank head surface 34 forces outward movement of the retainer 12 towards the cylindrical surface 99 defining the receiver expansion recess or chamber as best shown in FIG. 33, with the retainer spring tabs 118 remaining in an inwardly pressed position at the grooves 147 that are captured at the receiver surfaces 97. At this time, the spherical surface 34 of the head 8 is in contact with the surface 130 of the retainer 12. FIG. 34 illustrates the widening of the slit 136 defined by the surfaces 152 and 153 during expansion of the retainer 12 about the shank head 8. FIG. 34 also illustrates the position of the spring tabs 18 abutting against the insert surfaces 178 and 179 during expansion of the retainer 12 about the shank head 8, the head 8 hemisphere being shown in dotted lines. With reference to FIG. 35, the retainer 12 begins to return towards a neutral or nominal state as the center of the sphere of the head passes beyond the retainer surface 130. At this time, the spherical surface 34 moves into engagement with the inner upper rim surfaces 133 of the retainer 12 while the surface 34 remains in contact with at least an edge of the lower cylindrical surface 130. The combination of the rim 133 surface contact and the lower surface 130 contact (that each define a terminal portion of the smaller radiused surface 132), both resiliently pressing against the larger radiused surface 34, provides a fairly tight friction fit between the head 8 and the retainer 12, the surface 34 being pivotable with respect to the retainer 12 with some force. Thus, a tight, non-floppy ball and socket joint is now created between the retainer 12 and the shank upper portion 8.

Figure 36:
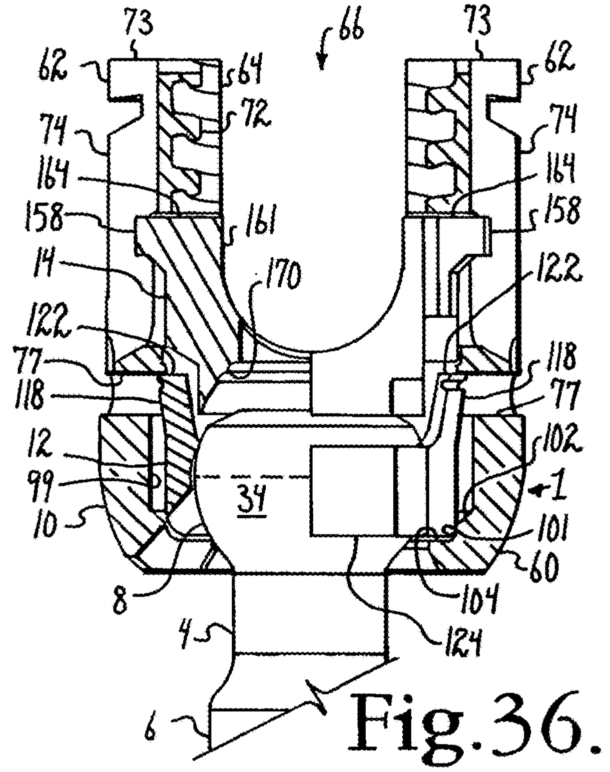
FIG. 36 is a partial front elevational view with portions broken away, similar to FIG. 35, the shank upper portion with attached retainer being shown pulled down into a partially seated position within the lower receiver cavity, the retainer spring tabs in a substantially neutral state, extending outwardly partially into receiver apertures.

With reference to FIG. 36, the receiver is then pulled upwardly or the shank 4 and attached retainer 12 are then moved manually downwardly into a position wherein the retainer spring tab 118 grooves 147 are disengaged from the receiver surfaces 97, allowing the tabs 118 to resiliently extend outwardly into a neutral or near-neutral position, slightly extending into each of the receiver through apertures 77. It is foreseen that in some embodiments of the invention, an upper portion of the aperture 77 may include a wall or a recessed surface may be formed in the receiver directly above the aperture 77, to provide for a temporary abutment surface for the spring tabs 118 during angular manipulation of the shank with respect to the retainer and receiver, but prior to final locking of the shank with respect to the receiver, in order to further increase the friction fit relationship between the shank and the retainer during surgery.

Figure 37:
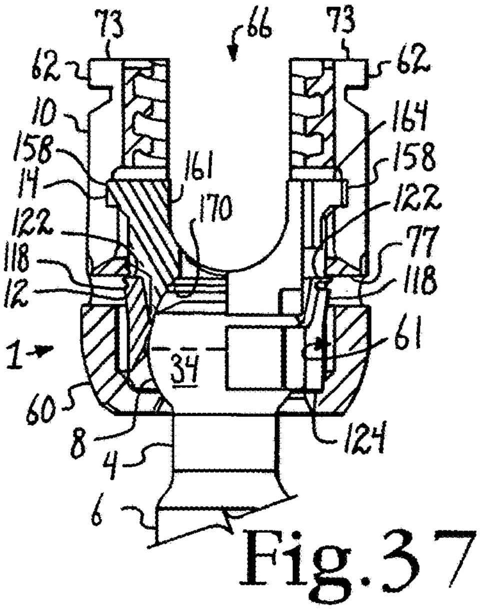
FIG. 37 is a reduced and partial front elevational view with portions broken away, similar to FIG. 36, the insert being shown in a position dropped down on the retainer spring tabs.

With further reference to FIGS. 36 and 37, after the retainer 12 is moved downwardly into the receiver 10, the insert 14 also moves downwardly into engagement with the retainer 12 (FIG. 37). However, at this time, the retainer 12 may not yet be seated on the receiver seating surface 104. As shown in FIGS. 36 and 37, it has been found that the resilient retainer 12 may not return to an original nominal or neutral state that the retainer 12 was in prior to expansion about the shank head 8 and thus may be spaced from the receiver surface 104 and not easily pressed into a desired seated position. In situations wherein the slit 136 of the retainer requires additional force to return to the original pre-expansion state, a tool (not shown) having opposed prongs or arms is received in the opposed receiver slots or outer grooves 74 and moved downwardly into abutment with the exposed top surfaces 164 of the insert wings 158. With reference to FIG. 38, the insert 14 at the sloping surfaces 178 is then pressed downwardly by such a tool into engagement with inner surfaces 149 of the retainer spring tabs 118, and the insert 14 and the retainer 12 may then be forced downwardly until the retainer bottom surface 124 abuts against the receiver seat 104, the retainer 12 being pressed inwardly along the sloping surface or surfaces 102. At this time, the retainer spring tabs 118 are spread slightly further outwardly into the receiver bores 77, making it impossible to move the retainer out of the locking portion of the receiver chamber defined in part by the receiver seat 104 unless pressed inwardly by a tool or tools via the through bores 78. In some embodiments, when the receiver 10 is pre-assembled with the shank 4, the entire assembly 1 may be implanted at this time by inserting the driving tool (not shown) into the receiver and the shank drive 46 and rotating and driving the shank 4 into a desired location of the vertebra 17. With reference to FIG. 38 and also, for example, to FIGS. 41-46, at this time, prior to locking with a closure top, the receiver 10 may be articulated to a desired angular position with respect to the shank 4, such as that shown in FIG. 54, that will be held, but not locked, by the frictional engagement between the retainer 12 and the shank upper portion 8. With further reference to FIG. 38 and also FIG. 39, the insert 14 may be pressed downwardly into locking engagement with the shank head 8 by a tool further pressing on the wings 158 as previously described herein or by the rod 21 and the closure top 18.

With reference to FIGS. 39 and 40, the rod 21 is eventually positioned in an open or percutaneous manner in cooperation with the at least two bone screw assemblies 1. The closure structure 18 is then advanced between the arms 62 of each of the receivers 10. The closure structure 18 is rotated, using a tool engaged with the inner drive 186 until a selected pressure is reached at which point the rod 21 engages the U-shaped seating surface 162 of the compression insert 14, further pressing the insert spherical surface 168 and stepped shank gripping surfaces 170 against the shank spherical surface 34, the edges of the stepped surfaces 170 penetrating into the spherical surface 34 (see also FIGS. 43 and 45), pressing the shank upper portion 8 into locked frictional engagement with the retainer 12. Specifically, as the closure structure 18 rotates and moves downwardly into the respective receiver 10, the point 189 and rim 190 engage and penetrate the rod surface 22, the closure structure 18 pressing downwardly against and biasing the rod 21 into compressive engagement with the insert 14 that urges the shank upper portion 8 toward the retainer 12 and into locking engagement therewith, the retainer 12 frictionally abutting the surface 104 and pressing outwardly against the cylindrical surface 101. For example, about 80 to about 120 inch pounds of torque on the closure top may be applied for fixing the bone screw shank 6 with respect to the receiver 10. If disassembly if the assembly 1 is desired, such is accomplished in reverse order to the procedure described previously herein for assembly.

Figure 41:
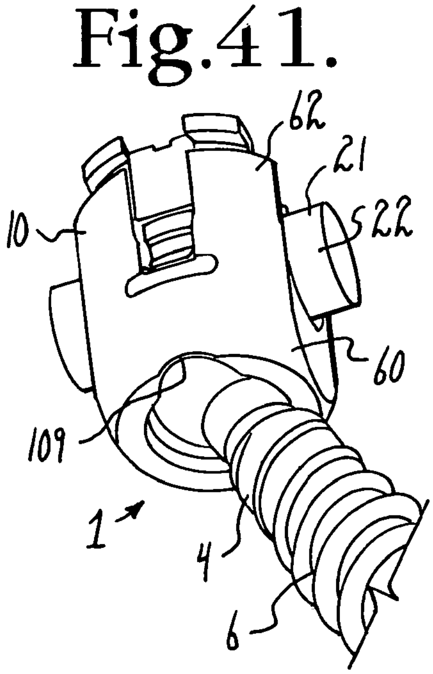
FIG. 41 is a reduced and partial perspective view of the assembly of FIG. 40, but with the shank shown disposed at about a twenty-five degree (caudad) angle with respect to the receiver.
Figure 42:
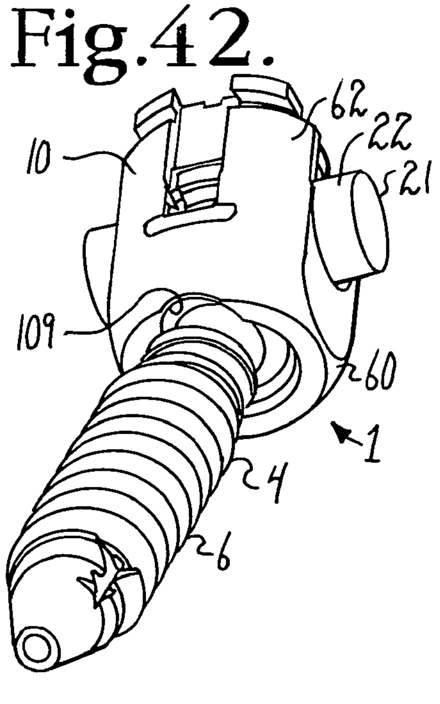
FIG. 42 is a reduced and partial perspective view of the assembly of FIG. 40, but with the shank shown disposed at about a twenty-five degree (medial) angle with respect to the receiver.
Figure 43:
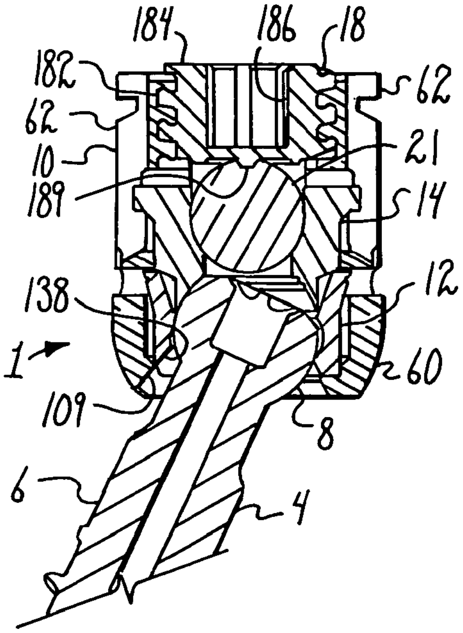
FIG. 43 is a partial front elevational view of the assembly as shown in FIG. 42 with portions broken away to show the detail thereof.
Figure 46:
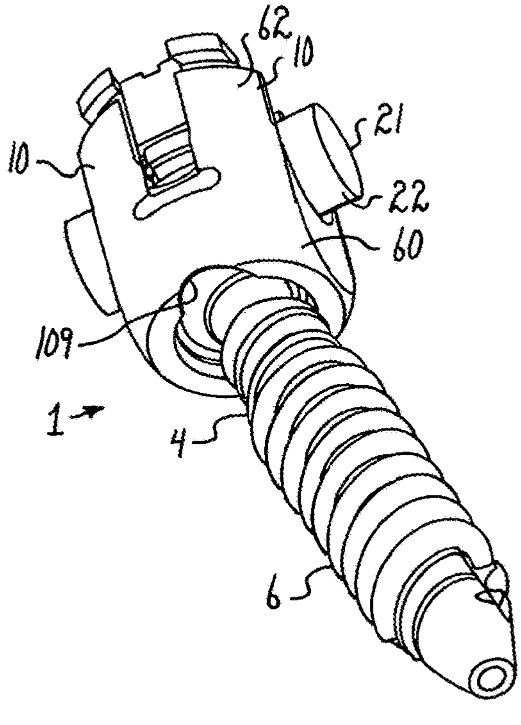
FIG. 46 is a reduced and partial perspective view of the assembly of FIG. 40, but with the shank shown disposed at about a twenty-five degree (multi-plane) angle with respect to the receiver.

With reference to FIGS. 41-46, different angular or articulated positions of the shank 4 with respect to the receiver 10 are shown, some making full use of the aligned cooperating cut-out or cupped surfaces 109 and 138 of the respective receiver 10 and retainer 12. For example, FIGS. 41 and 46 illustrate arrangements wherein the shank is pivoted in a direction away from the cooperating surfaces 109 and 138. Specifically, FIG. 41 illustrates a twenty-five degree caudad articulation, while FIG. 46 illustrates a multi-planar articulation that does not utilize the cupped surfaces for increased angulation. FIGS. 42 and 43 represent a twenty-five degree medial articulation, while FIGS. 44 and 45 show a forty degree medial articulation, illustrating either end of a wide range of angulations or articulations greater than twenty-five degrees possible with bone screw assemblies of the invention.

With reference to FIGS. 47-48, an alternative retainer 12A is illustrated for use with the shank 4, receiver 10, insert 14 closure top 18 and rod 21 previously described herein. The retainer 12A is identical to the retainer 12 with the exception that the retainer 12A does not include any vertically extending outer grooves 144.

With reference to FIGS. 49-50, an alternative retainer 12B is illustrated for use with the shank 4, receiver 10, insert 14 closure top 18 and rod 21 previously described herein. The retainer 12BA is identical to the retainer 12 with the exception that the retainer 12B includes only one outer vertically groove 144B located generally opposite a slit 136B.

Figure 51:
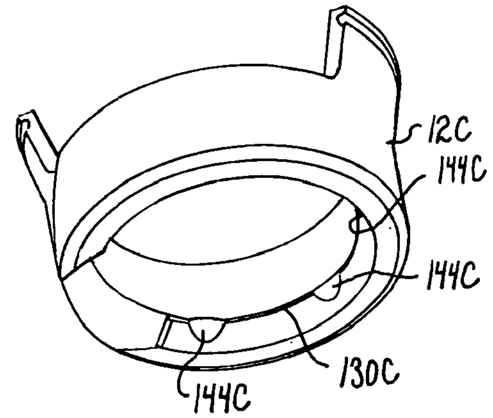
FIG. 51 is an enlarged perspective view of another alternative retainer according to the invention for use with the assembly of FIG. 1.
Figure 52:
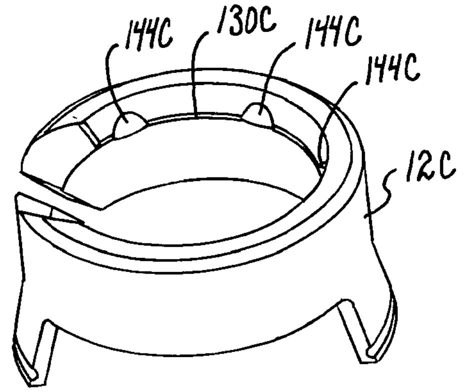
FIG. 52 is another enlarged perspective view of the retainer of FIG. 51.

With reference to FIGS. 51-52, an alternative retainer 12C is illustrated for use with the shank 4, receiver 10, insert 14 closure top 18 and rod 21 previously described herein. The retainer 12A is identical to the retainer 12 with the exception that the retainer 12A does not include any vertically extending outer grooves 144. Rather, the retainer 12C includes a plurality of inner notches 144C located at or near an inner rim or cylindrical surface 130C that is otherwise identical to the inner cylindrical surface 130 of the retainer 12.

Figure 53:
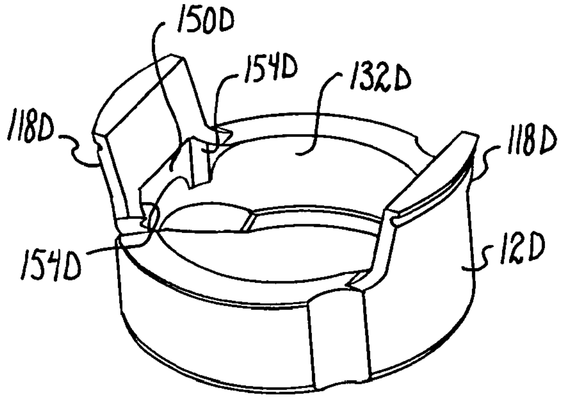
FIG. 53 is an enlarged perspective view of another alternative retainer according to the invention for use with the assembly of FIG. 1.
Figure 54:
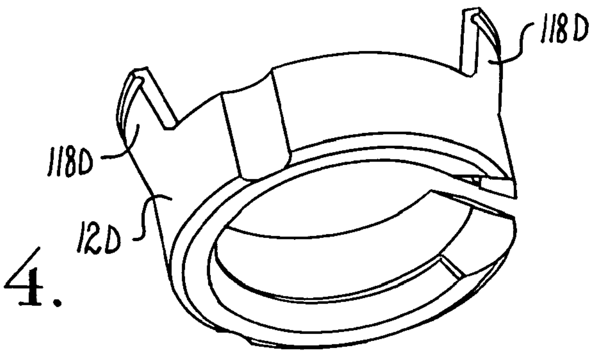
FIG. 54 is another enlarged perspective view of the retainer of FIG. 53.

With reference to FIGS. 53-54, an alternative retainer 12D is illustrated for use with the shank 4, receiver 10, insert 14 closure top 18 and rod 21 previously described herein. The retainer 12D is identical to the retainer 12 with the exception that the retainer 12D further includes a pair of inner expansion relief cut-outs 154D located below and at either side of each spring tab 118D. The cut-outs 154D are formed in tab lower 150D and extend into an inner spherical surface 132D that is otherwise identical to the surface 132 of the retainer 12.

With reference to FIGS. 55-58, an alternative lock-and-release compression insert 214 is illustrated for use with the shank 4, receiver 10, retainer 12, closure top 18 and rod 21 previously described herein. The insert 214 is substantially similar to the insert 14 previously described herein, having all the features of the insert 14 and further including the additional feature of an outer locking surface 374, sized and shaped for a locking interference fit with a surface of the receiver, such as the cylindrical surface 95, and opposed manipulation slots 380 for use during locking and unlocking of the insert 214 with respect to the receiver surface 95.

Thus, the insert 214 includes the lower arm surface 374 that is similar to the arm surface 174 of the insert 14 with the exception that the cylindrical surface 374 is sized for a locking interference fit with the receiver inner cylindrical surface. In other words, a diameter of the surface 374 is sized large enough to require that the cylindrical surface 374 must be forced into the cylindrical surface 95 (or other receiver surface) by a tool or tools or by the closure top 18 forcing the rod 21 downwardly against the insert 214 with sufficient force to interferingly lock the insert 214 into the receiver 10. The insert is otherwise assembled with the receiver 10, retainer 12, shank 4, rod 21 and closure top 18 in a manner the same as previously described above with respect to the assembly 1, with the exception that the insert 214 must be forced downwardly into a locking interference fit with the receiver 10 when the shank 4 is locked in place, as compared to the easily sliding relationship between the insert 14 and the receiver 10. For example, the surfaces 374 and 95 may be sized such that the insert 214 is prohibited from moving any further downwardly at the beginning of the surface 95 unless forced downwardly by a locking tool or by the closure top pressing downwardly on the rod that in turn presses downwardly on the insert 214. Once the insert 214 is locked against the receiver, the closure top 18 may be loosened or removed and/or the rod 21 may be adjusted and/or removed and the frictional engagement between the insert 214 and the receiver 10 at the receiver surface 95 will remain locked in place, advantageously maintaining a locked angular position of the shank 4 with respect to the receiver 10. At such time, another rod, such as the deformable rod and cooperating alternative closure top may be loaded onto the already locked-up assembly to result in an alternative assembly.

If unlocking of the insert 214 with respect to the receiver 10 is desired, a tool (not shown) may be inserted into the slots 380 and the insert 14 may be pulled away from the receiver 10. Such a tool may include a piston-like portion for pushing directly on the shank while the insert 14 is pulled away from the receiver. In other embodiments, or applications where a rod and closure top are still engaged with the receiver 10, a tool (not shown) may be used to engage and pull up on the insert wings that extend through the receiver apertures 83. At such time, the shank 4 may be articulated with respect to the receiver 10, and the desired friction fit returns between the retainer 12 and the shank surface 34, so that an adjustable, but non-floppy relationship still exists between the shank 4 and the receiver 10. If further disassembly if the assembly is desired, such is accomplished in reverse order to the procedure described previously herein for the assembly 1.

It is to be understood that while certain forms of the present invention have been illustrated and described herein, it is not to be limited to the specific forms or arrangement of parts described and shown.

What is claimed is:

1. A receiver of a bone anchor intended for securing a rod to the bone anchor with a closure top, the receiver comprising:

a receiver body having a longitudinal axis, a base portion, and a pair of upright arms extending upwardly from the base portion to define an open channel configured to receive the rod, the open channel having a transverse axis perpendicular to the longitudinal axis and opening through front and back faces of the upright arms having outer edges spaced from the open channel, the upright arms having top surfaces defining a top of the receiver body, opposed interior surfaces including a discontinuous guide and advancement structure adjacent the top surfaces configured to mate with the closure top, and exterior side surfaces opposite the opposed interior surfaces extending downward across the base portion towards a bottom of the receiver body and extending horizontally to the outer edges of the front and back faces of the upright arms;

a horizontally-elongate upper tool-engaging groove formed into the exterior side surface of each upright arm, the upper tool-engaging groove being proximal to and below a top surface of the upright arm and extending horizontally to the outer edges of the front and back faces of each upright arm, the upper tool-engaging groove including a downwardly-facing upper surface, an opposed upwardly-facing lower surface, and an outwardly-facing inner surface therebetween; and a tool-engaging recess extending across the upper tool-engaging groove of each upright arm, the tool-engaging recess extending upwardly through the downwardly-facing upper surface and downwardly through the upwardly-facing lower surface of the upper tool-engaging groove and including an outwardly-facing planar surface opposite and parallel to an outwardly-facing planar surface of the tool-engaging recess of the other upright arm.

2. The receiver of claim 1, wherein the tool-engaging recess extends into the outwardly-facing inner surface of the upper tool-engaging groove.

3. The receiver of claim 1, wherein the upper tool-engaging groove of each upright arm is curvate to extend at least partially circumferentially around a periphery of the upright arm.

4. The receiver of claim 1, wherein both the front face and the back face of each upright arm further comprises at least one planar surface between outer edges and the open channel, and wherein at least the downwardly-facing upper surface of the upper tool-engaging groove of the upright arm extends through the outer edges and opens onto the at least one planar surface of both the front face and the back face of the upright arm.

5. The receiver of claim 1, wherein the tool-engaging recess extends across a center portion of the upper tool-engaging groove.

6. The receiver of claim 1, wherein the downwardly-facing upper surface of each upper tool-engaging groove further comprises an undercut or dovetail.

7. The receiver of claim 1, wherein the upwardly-facing lower surface of each upper tool-engaging groove extends outwardly and downwardly from a lower corner of the outwardly-facing inner surface.

8. The receiver of claim 1, wherein the upper tool-engaging grooves are located entirely above the rod when the rod is secured in the open channel by the closure top.

9. The receiver of claim 1, wherein the tool-engaging recesses extend downwardly below the upper tool-engaging grooves to intersect with side apertures extending through a thickness of the upright arms below the discontinuous guide and advancement structure.

10. A bone anchor assembly intended for securing a rod to a bone of a patient, the bone anchor assembly comprising:

a receiver comprising a longitudinal axis, a lower portion, and an upper portion including pair of upright arms extending upwardly from the lower portion to define an open channel configured to receive the rod, the open channel having a transverse axis perpendicular to the longitudinal axis and opening through front and back faces of the upright arms having outer edges spaced from the open channel, the upright arms having top surfaces defining a top of the receiver, opposed interior surfaces including a discontinuous guide and advancement structure adjacent the top surfaces configured to mate with a closure top, and exterior side surfaces opposite the opposed interior surfaces extending downward across the lower portion towards a bottom of the receiver and extending horizontally to the outer edges of the front and back faces of the upright arms;

a horizontally-elongate upper tool-engaging groove formed into the exterior side surface of each upright arm, the upper tool-engaging groove being adjacent to and below a top surface of the upright arm and extending horizontally to the outer edge of at least one of the front face or the back face of the upright arm, the upper tool-engaging groove including a downwardly-facing upper surface, an opposite upwardly-facing lower surface, and an outwardly-facing inner surface therebetween;

a tool-engaging recess extending entirely across the upper tool-engaging groove of each upright arm, the tool-engaging recess extending upwardly through the downwardly-facing upper surface and downwardly through the upwardly-facing lower surface of the upper tool-engaging groove and including an outwardly-facing planar surface opposite and parallel to an outwardly-facing planar surface of the tool-engaging recess of the other upright arm; and a bone anchor extending downwardly from the receiver, the bone anchor having an anchor portion configured for attachment to the bone of the patient.

11. The bone anchor assembly of claim 10, wherein the bone anchor further comprises a shank having a head portion opposite the anchor portion configured to be pivotally received within the lower portion of the receiver.

12. The bone anchor assembly of claim 11, wherein the shank is cannulated by having a central opening extending along an entire length thereof.

13. The bone anchor assembly of claim 11 and further comprising an insert having a lower surface configured to apply pressure to the head portion of the shank and an upper surface configured for engagement by one of the rod or a tool.

14. The bone anchor assembly of claim 13, wherein the insert is configured to be top loaded into the receiver.

15. The bone anchor assembly of claim 13, wherein the receiver includes a non-threaded internal recess spaced above a lower opening in the receiver and having downwardly-facing internal surface configured to overlappingly receive an upwardly-facing outer surface on the insert.

16. The bone anchor assembly of claim 15, wherein the internal recess is radiused.

17. The bone anchor assembly of claim 16, wherein the tool-engaging recesses extend downwardly below the upper tool-engaging grooves to intersect with side apertures extending through a thickness of the upright arms below the discontinuous guide and advancement structure.

18. The bone anchor assembly of claim 13, wherein the insert includes a central bore configured to allow passage of a driving tool to engage an internal drive aperture formed in the head portion of the shank.

19. The bone anchor assembly of claim 10, wherein the closure top includes a continuous guide and advancement structure formed into an outer sidewall surface configured to engage the discontinuous guide and advancement structure formed into the opposed interior surfaces of the upright arms to capture the rod within the open channel of the receiver.

20. The bone anchor assembly of claim 19, wherein the closure top is positioned inwardly within the receiver with respect to the upper tool-engaging grooves to engage the rod.

21. A receiver of a bone anchor intended for securing a rod to the bone anchor with a closure top, the receiver comprising:

a receiver body having a longitudinal axis, a base portion, and a pair of upright arms extending upwardly above the base portion to define an open channel configured to receive the rod, the open channel having a transverse axis perpendicular to the longitudinal axis and opening through front faces and back faces of the upright arms comprising outer edges spaced from the open channel, both the front faces and the back faces including at least one pair of planar surfaces between the outer edges and the open channel, the upright arms having top surfaces defining a top of the receiver body, opposed interior surfaces including a discontinuous guide and advancement structure adjacent the top surfaces configured to mate with the closure top, and exterior side surfaces opposite the opposed interior surfaces extending downward across the base portion towards a bottom of the receiver body and extending horizontally to the outer edges of both the front faces and the back faces of the upright arms;

a horizontally-elongate upper tool-engaging notch formed into the exterior side surface of each upright arm, the upper tool-engaging notch being proximal to and below a top surface of the upright arm and extending horizontally to and through the outer edge of at least one of the front face or the back face of the upright arm to open into one of the at least one pair of planar surfaces, the upper tool-engaging notch including a downwardly-facing upper surface and an outwardly-facing inner surface; and a tool-engaging recess extending into the upper tool-engaging notch of each upright arm and including an outwardly-facing planar surface opposite and parallel to an outwardly-facing planar surface of the tool-engaging recess of the other upright arm.

22. The receiver of claim 21, wherein the discontinuous guide and advancement surface comprises one of a helically wound flange, a reverse angle thread, a buttress thread, or a square thread.

23. The receiver of claim 21, wherein the at least one pair of planar surfaces of the front faces and the back faces of the upright arms extend perpendicular to the transverse axis of the open channel.

24. The receiver of claim 21, wherein the upper tool-engaging notch of each upright arm is curvate to extend at least partially circumferentially around a periphery of the upright arm.

25. The receiver of claim 21, wherein the upper tool-engaging notch of each upright arm extends to and through the outer edges of both the front face and the back face of the respective upright arm.

26. The receiver of claim 25, wherein the tool-engaging recess extends into a center portion of the upper tool-engaging notch.

27. The receiver of claim 21, wherein the downwardly-facing upper surface of each upper tool-engaging notch further comprises an undercut or dovetail.

28. The receiver of claim 21, wherein each upper tool-engaging notch further includes an upwardly-facing lower surface.

29. The receiver of claim 21, wherein the downwardly-facing upper surface of each upper tool-engaging notch is located entirely above the rod when the rod is secured in the open channel by the closure top.

30. The receiver of claim 21, wherein the tool-engaging recesses extend downwardly below the upper tool-engaging notches to intersect with side apertures extending through a thickness of the upright arms below the discontinuous guide and advancement structure.

31. A bone anchor assembly intended for securing a rod to a bone of a patient, the bone anchor assembly comprising:

a receiver body having a longitudinal axis, a base portion with a bottom opening, and a pair of upright arms extending upwardly from the base portion to define an open channel configured to receive the rod, the open channel having a transverse axis perpendicular to the longitudinal axis and opening through front faces and back faces of the upright arms having outer edges spaced from the open channel, both the front faces and the back faces including at least one pair of planar surfaces between the outer edges and the open channel, the upright arms having top surfaces defining a top of the receiver body, opposed interior surfaces including a discontinuous guide and advancement structure adjacent the top surfaces configured to mate with a closure top, and exterior side surfaces opposite the opposed interior surfaces extending downward across the base portion towards a bottom of the receiver body and extending horizontally to the outer edges of both the front faces and the back faces of the upright arms;

a horizontally-elongate upper tool-engaging groove cut into the exterior side surface of each upright arm, the upper tool-engaging groove being proximal to and below a top surface of the upright arm and extending horizontally to the outer edge of both the front face and the back face of each upright arm, the upper tool-engaging groove including a downwardly-facing upper surface, an opposite upwardly-facing lower surface, and an outwardly-facing inner surface therebetween; and a shank positionable within the base portion of the receiver body and having an integral spherically-shaped shank head opposite an anchor portion configured for implantation into the bone, wherein at least the downwardly-facing upper surface of the upper tool-engaging groove of each upright arm extends through the outer edges and opens onto the at least one planar surface of both the front face and the back face of the upright arm.

32. The bone anchor assembly of claim 31, wherein the receiver body further includes a tool-engaging recess extending across the upper tool-engaging groove of each upright arm, the tool-engaging recess extending upwardly through the downwardly-facing upper surface and downwardly through the upwardly-facing lower surface of the upper tool-engaging groove, and wherein each tool-engaging recess includes an outwardly-facing planar surface opposite and parallel to one another.

33. The bone anchor assembly of claim 31, wherein the at least one pair of planar surfaces between the outer edges and the open channel of both the front faces and the back faces of the upright arms extend perpendicular to the transverse axis of the open channel.

* * * * *